United States Patent
Osorio et al.

(10) Patent No.: US 11,026,622 B2
(45) Date of Patent: Jun. 8, 2021

(54) STATE CHANGE INDICATION BY MATCHING INSTANTANEOUS HEART RATE SHAPE TO SHAPE CHANGE TEMPLATE

(71) Applicant: Flint Hills Scientific, L.L.C., Lawrence, KS (US)

(72) Inventors: Ivan Osorio, Leawood, KS (US); Mark G. Frei, Leawood, KS (US)

(73) Assignee: FLINT HILLS SCIENTIFIC, L.L.C., Lawrence, KS (US)

(*) Notice: Subject to any disclaimer, the term of this patent is extended or adjusted under 35 U.S.C. 154(b) by 103 days.

(21) Appl. No.: 15/009,568

(22) Filed: Jan. 28, 2016

(65) Prior Publication Data

US 2016/0213271 A1 Jul. 28, 2016

Related U.S. Application Data

(63) Continuation of application No. 14/658,007, filed on Mar. 13, 2015, now Pat. No. 9,265,433, which is a
(Continued)

(51) Int. Cl.
*A61B 5/04* (2006.01)
*A61B 5/00* (2006.01)
(Continued)

(52) U.S. Cl.
CPC .......... *A61B 5/4094* (2013.01); *A61B 5/0245* (2013.01); *A61B 5/02405* (2013.01); *A61B 5/316* (2021.01); *A61B 5/349* (2021.01); *A61B 5/35* (2021.01); *A61B 5/352* (2021.01); *A61B 5/364* (2021.01); *A61B 5/7246* (2013.01);
*A61B 5/7275* (2013.01); *A61N 1/36053* (2013.01); *A61N 1/36064* (2013.01)

(58) Field of Classification Search
CPC ... A61B 5/0205; A61B 5/0402; A61B 5/0006; A61B 5/7246; A61B 5/7275; A61B 5/02405; A61B 5/0245; A61B 5/0452; A61B 5/7278; A61B 5/7235; A61B 5/7264; A61B 5/04012; A61B 5/7282; A61B 5/72; A61B 5/024; A61B 5/04525; A61B 5/7221; A61B 5/0468; A61B 5/00; A61B 5/486; A61B 5/6869; A61B 2562/227; A61B 5/0082; A61B 5/02; A61B 5/04011; A61B 5/04017; A61B 5/68; A61N 1/36585; A61N 1/3702; A61N 1/3621; A61N 1/37; A61N 1/365; A61N 1/36507; G06F 19/345; A61M 2230/04; A61M 2230/08; A61H 2230/04; A63B 2230/06

See application file for complete search history.

(56) References Cited

U.S. PATENT DOCUMENTS 3,768,014 A * 10/1973 Smith .................. G01R 23/10
324/76.48
4,154,238 A * 5/1979 Link .................. A61B 5/02208
600/494
(Continued)

*Primary Examiner* — Deborah L Malamud
(74) *Attorney, Agent, or Firm* — CF3; Stephen Eisenmann

(57) ABSTRACT

Methods, systems, and apparatus for detecting and/or validating a detection of a state change by matching the shape of one or more of an cardiac data series, a heart rate variability data series, or at least a portion of a heart beat complex, derived from cardiac data, to an appropriate template.

6 Claims, 21 Drawing Sheets

Related U.S. Application Data continuation of application No. 14/042,557, filed on Sep. 30, 2013, now Pat. No. 9,020,582, which is a continuation of application No. 12/884,051, filed on Sep. 16, 2010, now Pat. No. 8,571,643.

(51) Int. Cl.
| | |
|---|---|
| *A61B 5/024* | (2006.01) |
| *A61N 1/36* | (2006.01) |
| *A61B 5/35* | (2021.01) |
| *A61B 5/316* | (2021.01) |
| *A61B 5/349* | (2021.01) |
| *A61B 5/352* | (2021.01) |
| *A61B 5/364* | (2021.01) |
| *A61B 5/0245* | (2006.01) |

(56) References Cited

U.S. PATENT DOCUMENTS

| | | | |
|---|---|---|---|
| 7,225,013 B2 * | 5/2007 | Geva | A61B 5/04012 600/513 |
| 2007/0093721 A1 * | 4/2007 | Lynn | A61B 5/00 600/532 |
| 2007/0265536 A1 * | 11/2007 | Giftakis | A61B 5/0402 600/508 |

\* cited by examiner

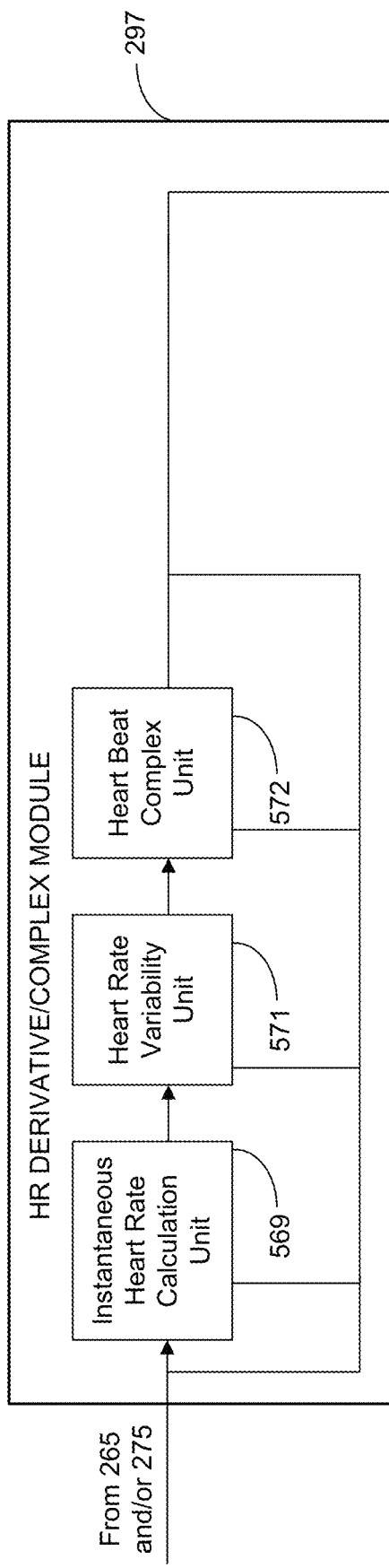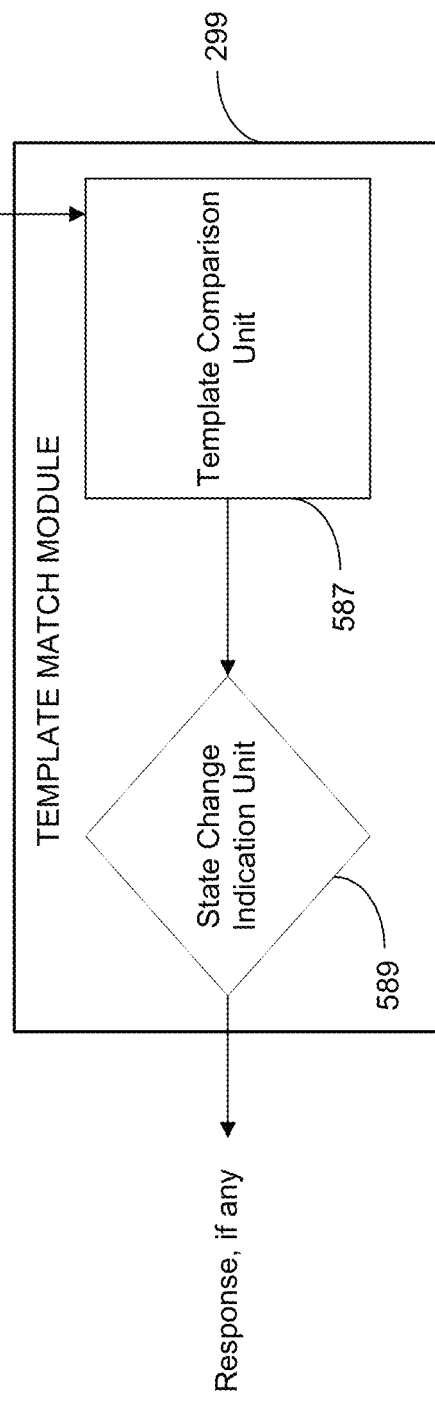

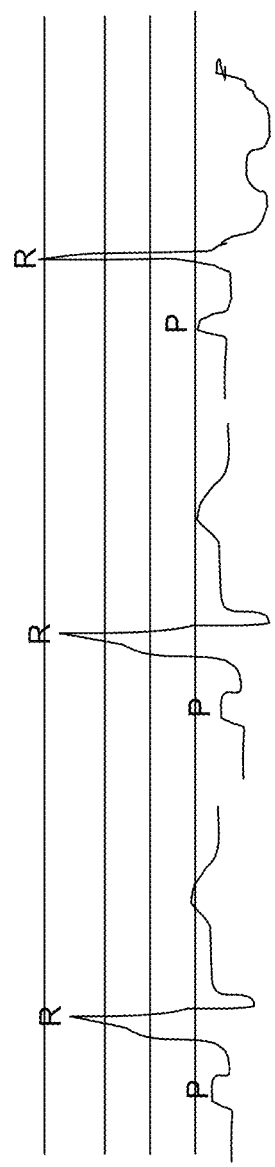

STATE CHANGE INDICATION BY MATCHING INSTANTANEOUS HEART RATE SHAPE TO SHAPE CHANGE TEMPLATE

CROSS-REFERENCE TO RELATED APPLICATIONS

This application is a Continuation of co-pending U.S. patent application Ser. No. 14/658,007 filed Mar. 13, 2015, which issued as U.S. Pat. No. 9,265,433, which is a Continuation of U.S. patent application Ser. No. 14/042,557, filed Sep. 30, 2013, which issued as U.S. Pat. No. 9,020,582 on Apr. 28, 2015; which is a Continuation of U.S. patent application Ser. No. 12/884,051, filed Sep. 16, 2010, which issued as U.S. Pat. No. 8,571,643 on Oct. 29, 2013. U.S. patent application Ser. No. 14/658,007 is incorporated by reference herein.

1. FIELD OF THE INVENTION

This invention relates to medical device systems and methods capable of detecting or validating a detection and, in some embodiments, treating an occurring or impending state change.

2. DESCRIPTION OF THE RELATED ART

Approximately 60 million people worldwide are affected with epilepsy, of whom roughly 23 million suffer from epilepsy resistant to multiple medications. In the USA alone, the annual cost of epilepsy care is USD 12 billion (in 1995 dollars), most of which is attributable to subjects with pharmaco-resistant state changes. Pharmaco-resistant state changes are associated with an increase mortality and morbidity (compared to the general population and to epileptics whose state changes are controlled by medications) and with markedly degraded quality of life for patients. State changes may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing.

Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, magnetic, electro-magnetic, photonic, acoustic, cognitive, and/or chemical signal to an organ or a neural structure in the patient's body. The signal is an exogenous signal that is distinct from the endogenous electro-chemical activity inherent to the patient's body and also from that found in the environment. In other words, the stimulation signal (whether electrical, mechanical, magnetic, electro-magnetic, photonic, acoustic, cognitive, and/or chemical in nature) applied to a cranial nerve or to other nervous tissue structure in the present invention is a signal applied from a medical device, e.g., a neurostimulator.

A "therapeutic signal" refers to a stimulation signal delivered to a patient's body with the intent of treating a medical condition through a suppressing (blocking) or modulating effect to neural tissue. The effect of a stimulation signal on neuronal activity may be suppressing or modulating; however, for simplicity, the terms "stimulating", suppressing, and modulating, and variants thereof, are sometimes used interchangeably herein. In general, however, the delivery of an exogenous signal itself refers to "stimulation" of an organ or a neural structure, while the effects of that signal, if any, on the electrical activity of the neural structure are properly referred to as suppression or modulation.

Depending upon myriad factors such as the history (recent and distant) of the nervous system, stimulation parameters and time of day, to name a few, the effects of stimulation upon the neural tissue may be excitatory or inhibitory, facilitatory or disfacilitatory and may suppress, enhance, or leave unaltered neuronal activity. For example, the suppressing effect of a stimulation signal on neural tissue would manifest as the blockage of abnormal activity (e.g., epileptic state changes) see Osorio et al., Ann Neurol 2005; Osorio & Frei IJNS 2009). The mechanisms thorough which this suppressing effect takes place are described in the foregeoing articles. Suppression of abnormal neural activity is generally a threshold or suprathreshold process and the temporal scale over which it occurs is usually in the order of tens or hundreds of milliseconds. Modulation of abnormal or undesirable neural activity is typically a "sub-threshold" process in the spatio-temporal domain that may summate and result under certain conditions, in threshold or suprathreshold neural events. The temporal scale of modulation is usually longer than that of suppression, encompassing seconds to hours, even months. In addition to inhibition or dysfacilitation, modification of neural activity (wave annihilation) may be exerted through collision with identical, similar or dissimilar waves, a concept borrowed from wave mechanics, or through phase resetting (Winfree).

In some cases, electrotherapy may be provided by implanting an electrical device, i.e., an implantable medical device (IMD), inside a patient's body for stimulation of a nervous tissue, such as a cranial nerve. Generally, electrotherapy signals that suppress or modulate neural activity are delivered by the IMD via one or more leads. When applicable, the leads generally terminate at their distal ends in one or more electrodes, and the electrodes, in turn, are coupled to a target tissue in the patient's body. For example, a number of electrodes may be attached to various points of a nerve or other tissue inside a human body for delivery of a neurostimulation signal.

Although non-contingent, programmed periodic stimulation (also referred to as "open-loop," "passive," or "non-feedback" stimulation (i.e., electrotherapy applied without reference to sensed information)) is the prevailing modality, contingent (also referred to as "closed-loop," "active," or "feedback" stimulation (i.e., electrotherapy applied in response to sensed information)) stimulation schemes have been proposed. Included in such proposed stimulation schemes are electrotherapy applied in response to an indication of an impending, occurring, or occurred state change, with the intent of reducing the duration, the severity, or both of a state change or a post-state change recovery period. However, such stimulation schemes would require reasonably sensitive techniques for indicating an impending, occurring, or occurred state change.

Even if closed-loop neurostimulation, or any other therapy for epilepsy, is not performed, reasonably sensitive and/or specific techniques for indicating an impending, occurring, or occurred state change would be desirable for warning of state changes to minimize risk of injuries and for logging to assess the state of the disease and assess the efficacy of therapies. Numerous studies have shown that self-reporting by patients, such as in state change diaries, generally only captures about half of all state changes having both electroencephalographic (EEG) and clinical signatures. Roughly a third of all patients do not identify any of their state changes. Detection of brain state changes may be accomplished using different body signals, but cortical electrical signals are most commonly used for this purpose. For multiple reasons (e.g., signal to noise ratio, stability of signals, etc.) intracranial and not scalp recordings are the modality of choice for prolonged (e.g., weeks to years) recording of cortical signals. However, since use of intracranial signals requires costly and burdensome surgical procedures that are associated with certain potentially serious complications, they are neither accessible nor acceptable to the majority of hundreds of thousands of patients that could benefit from them. Use of non-cerebral or extra-cerebral signals has emerged as a viable, useful, and highly cost-effective alternative to electrical cortical signals for the detection, warning, and logging of brain state changes, such as epileptic seizures.

SUMMARY OF THE INVENTION

In one aspect of the present invention, a method for indicating an occurrence of a state change is provided. In one aspect of the present invention, the method comprises obtaining a time series of cardiac data from a patient; determining a reference heart rate parameter from said cardiac data; determining a heart rate derivative shape from said time series of cardiac data, wherein said heart rate derivative shape comprises at least one characteristic selected from a number of phases relative to said reference heart rate parameter, a number of extrema of said heart rate derivative, a number of directions of change of said heart rate derivative, an area under the curve of at least one phase, a number of positive phases, or a number of negative phases; and indicating an occurrence of a state change based upon a determination that said heart rate derivative shape matches a state change template in said at least one characteristic, wherein said at least one characteristic of said state change template comprises two or more phases relative to said reference heart rate parameter, two or more extrema of said heart rate derivative, three or more directions of change of said heart rate derivative, a number of positive phases, or a number of negative phases, provided the total number of positive phases and negative phases is two or more.

In another aspect of the present invention, a method for indicating an occurrence of a state change is provided. In one aspect of the present invention, the method comprises obtaining data relating to at least a portion of a heart beat complex from a patient; comparing said at least said portion of said heart beat complex with a corresponding portion of a reference heart beat complex template of said patient; and indicating an occurrence of a state change based upon a determination that said heart beat complex fails to match said reference heart beat complex template.

In yet another aspect of the present invention, a computer readable program storage device is provided that is encoded with instructions that, when executed by a computer, perform a method described above.

In one aspect of the present invention, a medical device is provided comprising a computer readable program storage device as described above.

BRIEF DESCRIPTION OF THE DRAWINGS

The invention may be understood by reference to the following description taken in conjunction with the accompanying drawings, in which like reference numerals identify like elements, and in which:

FIG. 3C is a stylized block diagram of a HR derivative/complex module of a medical device, in accordance with one illustrative embodiment of the present invention;

FIG. 3D is a stylized block diagram of a template match module of a medical device, in accordance with one illustrative embodiment of the present invention;

FIG. 18 shows exemplary heart beat complex changes detectable by use of the P wave and the R wave of a heart beat, in accordance with an illustrative embodiment of the present invention.

Figure 1:
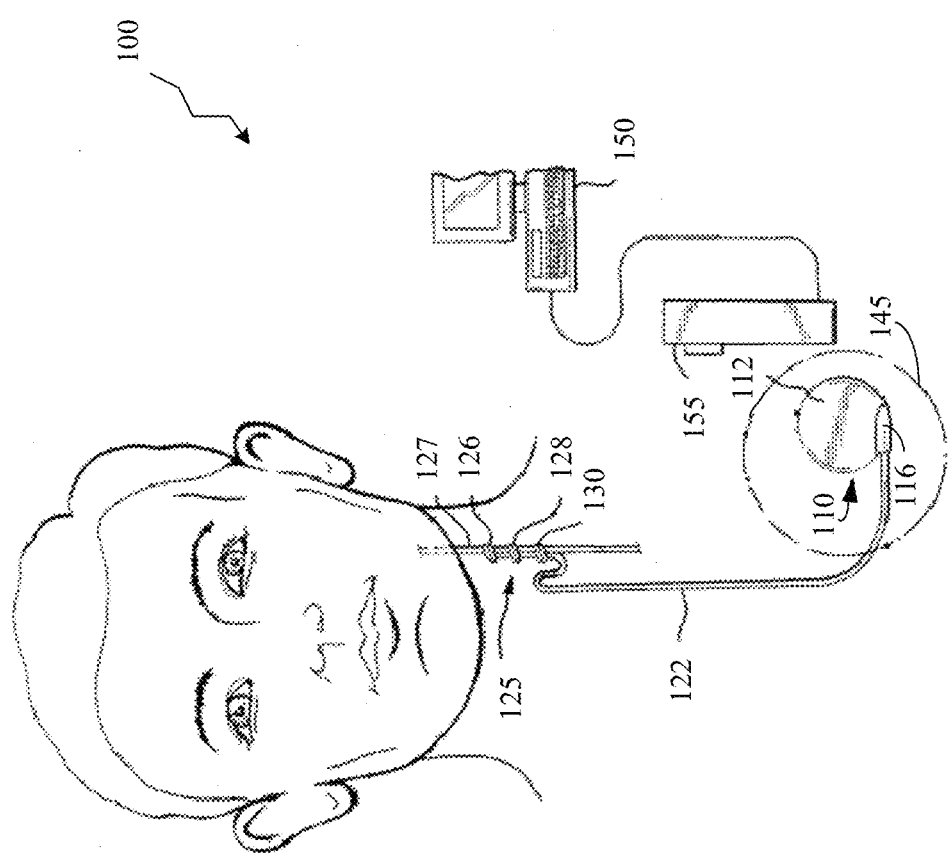
FIG. 1 provides a stylized diagram of a medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering a therapeutic signal generated by an IMD to a tissue), sensing electrodes (i.e., electrodes for sensing a physiological indication of a state of a patient's body), and/or electrodes that are capable of delivering a therapeutic signal, as well as performing a sensing function.

In one embodiment, the present invention provides a method of detecting a state change based upon data derivable from cardiac signals. The state change can be, for example, at least one of an unstable brain state, a brain state indicative of an elevated probability of a state change, a brain state indicative of an impending state change, or a state change, among others.

In one embodiment, the present invention provides a method for indicating an occurrence of a state change. In one embodiment, the method comprises obtaining a time series of cardiac data from a patient; determining a reference heart rate parameter from said cardiac data; determining a heart rate derivative shape from said time series of cardiac data, wherein said heart rate derivative shape comprises at least one characteristic selected from a number of phases relative to said reference heart rate parameter, a number of extrema of said heart rate derivative, a number of directions of change of said heart rate derivative, a number of positive phases, or a number of negative phases; and indicating an occurrence of a state change based upon a determination that said heart rate derivative shape matches a state change template in said at least one characteristic.

The cardiac data can be gathered by any of a number of techniques. For example, the cardiac data may be gathered by an electrocardiogram (EKG) device. For another example, the cardiac data may be gathered by a cranial nerve stimulator device. In one embodiment, the cardiac data may be related to the R-waves of the beat sequence, such as a time series of R-waves or a series of R-R intervals. Those skilled in the art having benefit of the present disclosure would appreciate that other time series of cardiac waves and/or their fiducial points (e.g., P waves, T waves, etc.) may be used and still remain within the spirit and scope of the present invention.

Data relating to R-waves may be gathered by an EKG device or, in one embodiment, by a vagus nerve stimulator, such as described in U.S. Pat. No. 5,928,272, which is hereby incorporated by reference herein.

Obtaining the cardiac data may comprise sensing a time of beat sequence of a patient's heart and generating a time series data stream from the time of the beat sequence. In a further embodiment, receiving the cardiac data of the patient's heart may comprise sensing and time-stamping a plurality of R waves, and generating the time series data stream may comprise determining a series of R-R intervals from the time stamps of the sensed R waves.

In one embodiment, the fiducial time marker is an R wave peak or threshold crossing. The amplitude or height of one or more representative R waves may be used to set a threshold that, when reached or crossed, is registered as a fiducial time marker of a heart beat.

In one embodiment, a heart rate derivative is determined from the time series of cardiac data. As defined herein, a "heart rate derivative" is a value derivable, directly or indirectly, from the time series of cardiac data, wherein the value relates to a feature, property or relationship between two or more heart beats. Although a first or higher-order derivative, as understood from calculus, is a "heart rate derivative" under the above definition, a heart rate derivative is not necessarily a first or higher-order calculus derivative. Exemplary heart rate derivatives include, but are not limited to, heart rate and heart rate variability (HRV). A "shape" is used herein to refer to a feature apparent to the person of ordinary skill in the art upon viewing a graph of the heart rate or of one of its derivative over a period of time. In one embodiment, a heart rate derivative shape comprises at least one characteristic selected from a number of phases relative to a reference heart rate parameter, a number of extrema of the heart rate derivative, a number of directions of change of the heart rate derivative, a number of positive phases, or a number of negative phases.

By "heart rate shape" is meant one or more characteristics or features of a time series of cardiac data that are reflective of the appearance of that time series if plotted on a graph (on the y-axis and time on the x-axis). For example, one characteristic of heart rate shape is a number of phases relative to the reference heart rate parameter. A "phase" is a period between two consecutive deviations from, crossings of, or returns to the reference heart rate parameter. A phase may be positive (having a value greater than the reference heart rate parameter) or negative (having a value less than the reference heart rate parameter). Yet another exemplary characteristic of heart rate shape is a number of extrema of heart rate. An "extremum" (plural, "extrema") is a point where the slope of heart rate changes sign, or phrased alternatively, a point that is a highest high or lowest low of heart rate for some length of time or number of beats before and after. Still another exemplary characteristic of heart rate shape is a number of directions of heart rate change, which can be defined as the number of changes of the sign of the slope of heart rate, plus one. Yet another exemplary characteristic of heart rate shape is the steepness of one or more ascending or descending slopes.

Though not to be bound by theory, we have found that heart activity during normal states (exercise, anger, etc.) and abnormal states (e.g., epileptic seizures) as displayed or graphed over various time scales take on distinctive shapes which may be used to identify the various states as well as changes from one state to another, such as from non-seizure to seizure. Said shapes are considered and treated herein as templates, given their stereotypical nature, and are used in several ways (to be described below) to detect states, state changes, state and/or state change onsets, and/or other features, such as duration, intensity or magnitude, and/or other relevant characteristics, such as type of state or state change.

Another heart rate derivative that may be considered is a heart rate volatility (non-stationarity) parameter, a measure of dispersion which may be defined as a change in the standard deviation or variance of heart rate over a moving window. Commonly, the higher the volatility, the higher appears to be the probability of state changes. Volatility, a metric often found in financial contexts, is used here to obtain certain information about the state of a system regardless of the similarities or dissimilarities between financial and biological time series and consideration for the underlying systems' dynamics.

For example, let $\ldots {}^{t-2}Q, {}^{t-1}Q, {}^{t}Q, {}^{t+1}Q, \ldots$ be a stochastic process. Its terms ${}^{t}Q$ represent heart rates as components of a vector or a matrix. The volatility of the process at time $t^{-1}$ is defined as the standard deviation of the time t return. Typically, log returns are used, so the definition becomes $$\text{volatility} = std\left(\log\left(\frac{{}^{t}Q}{{}^{t-1}Q}\right)\right) \quad [1]$$

wherein log denotes a natural logarithm.

If heart rate time series are conditionally homoskedastic, definition [1] is precise. However, if they are conditionally heteroskedastic, measure [1] requires modification. Volatility at time $t^{-1}$ represents in this case, the standard deviation of the time t log return conditional on information available at time $t^{-1}$ as defined below $$\text{volatility} = {}^{t-1}std\left(\log\left(\frac{{}^{t}Q}{{}^{t-1}Q}\right)\right)$$

wherein the preceding superscript $t^{-1}$ indicates that the standard deviation is conditional on information available at time $t^{-1}$.

Transitions from homoskedasticity (defined herein as approximately constant standard deviations over a certain time window) to heteroskedasticity (inconstant standard deviation) also provide information about the probability of being in or near a state change of interest and may be used for automated detection, warning, delivery of therapy and logging (of events, warnings and therapy) purposes.

Volatility will be measured using time scales (seconds to days) based on temporal (e.g., duration) and other properties of the state change on interest and of the reference state.

The method also comprises indicating an occurrence of a state change based upon a determination that said heart rate derivative shape matches a state change template in said at least one characteristic.

A "state change template" is a template known or discovered by the practitioner to be associated with the state change, wherein the template can be used in the analysis of the heart rate derivative shape.

Plots of instantaneous heart rate (y-axis) as a function of time (x-axis) in subjects with epilepsy reveal consistent changes before, during and after seizures, referred herein to as circum-ictal changes. ("Circum-ictal" or "circumictal," as used herein, encompasses pre-ictal, ictal, and post-ictal subperiods. The circumictal period can be considered the time window (e.g., in min) preceding and following a seizure during which cardiac activity differs from that observed during interictal conditions, normal physical activity (including exercise), intense emotions (fear, anger, etc.), and physiological functions such as defecation, urination or coitus). The curves described by these circum-ictal changes in heart rate, approximate triangles or parabolae, and may have indentations of varying sizes. See the discussion of FIGS. 5-17B below for more information. Visual review of a large human database of instantaneous heart rate plots reveal that over a certain window length (referred herein as the mesoscopic scale) their circum-ictal shapes are limited to the triangles and parabolae and to "deformations" of these two shapes (see FIG. 5). These "deformations" appear to have temporal and magnitude dependencies, in that the longer the duration of the change in heart rate and the larger its magnitude, the more likely they are to occur. The behavior of these shapes likely reflect fluctuations in the strength of sympathetic and parasympathetic inputs to the heart. For example, transient, rapid drops in heart rate may be caused by either a withdrawal in sympathetic tone or by an increase in parasympathetic tone resulting from differential activation or inhibition by epileptiform activity of brain regions involved in autonomic control.

The shape (i.e., all the geometrical information that is invariant to position (including rotation) and scale) of these curves may be used for detection of changes in brain state such as epileptic seizures and their properties may be characterized through use of statistical shape analysis (e.g., Procrustes analysis), of the different embodiments of "matched filtering" or of other geometrical (Euclidian and non-Euclidian) methods. Other approaches such as computing the area of the triangles and parabolae and comparing the results to a reference value outside the circum-ictal state[ ] may be used. In the case of triangles, there area may be calculated using for example Heron's formula:

$\text{Area} = \sqrt{S(S-a)(S-b)(S-c)}$, where $S=\frac{1}{2}(a+b+c)$ and a, b, and c are the sides of the triangle.

Similarly the area of parabolae (Area=$\frac{2}{3}b \times h$, where b is the base and the height, may be computed and used to detect seizures.

Other attributes not captured by the concept of shape may be applied as need to the sign al for detecting state changes such as epileptic seizures.

In one embodiment, the at least one characteristic of the state change template comprises two or more phases relative to the reference heart rate parameter, two or more extrema of the heart rate derivative, three or more directions of change of the heart rate derivative or its slope, a number of positive phases, or a number of negative phases, provided the total number of positive phases and negative phases is two or more.

In another embodiment, the at least one characteristic of the state change template comprises at least one phase relative to the reference heart rate parameter, at least one extremum of the heart rate derivative or its slope, two or more directions of change of the heart rate derivative, a number of positive phases, or a number of negative phases, provided the total number of positive phases and negative phases is at least one.

In another embodiment, the at least one characteristic of the state change template comprises at least one of the amplitude of at least one phase, the duration of at least one phase, the valence (positive or negative) of at least one phase, at least one slope of at least one phase, the arc length (which is used interchangeably with line length) of at least one phase, the number of extrema in at least one phase, and the sharpness of the extrema of at least one phase.

A reference heart rate parameter, as used herein, is a reference value obtained during a state that is deemed of no or little interest for automated detection, warning, treatment or logging purposes. The reference heart rate parameter may be a single value, a series of values, a statistical is selected from the group consisting of a shape, a vector, a vector space, a matrix and two or more thereof.

For example, heart activity during a non-seizure state is considered as a reference state. The reference heart rate parameter may be calculated from a time series of value over any particular window, such as a window having a length from 30 sec to 24 hr, although longer or shorter windows may be used. The window may be a simple window or an exponentially-forgetting window, as discussed in U.S. patent application Ser. No. 12/770,562, filed Apr. 29, 2010; Ser. No. 12/771,727, filed Apr. 30, 2010; and Ser. No. 12/771,783, filed Apr. 30, 2010; the disclosures of each hereby incorporated herein by reference. The reference heart rate parameter may be calculated as any measure of any tendency of the time series, such as the central tendency of the time series. For example, the reference heart rate parameter may be calculated as a mean, median, nth percentile (where n can be from 30 to 70), or exponential moving average of the time series, among other measures of central tendency. Other mathematical or statistical measures, including, but not limited to, correlation dimension, entropy, Lyapunov exponents, and fractal or multifractal dimensions, may be also applied to any of the parameters or their templates.

The reference heart rate parameter may be determined from previously recorded data, or from "normative" values obtained from normal or abnormal cohorts of subjects or populations or it may be determined from the time series of cardiac data referred to above.

Figure 8A:
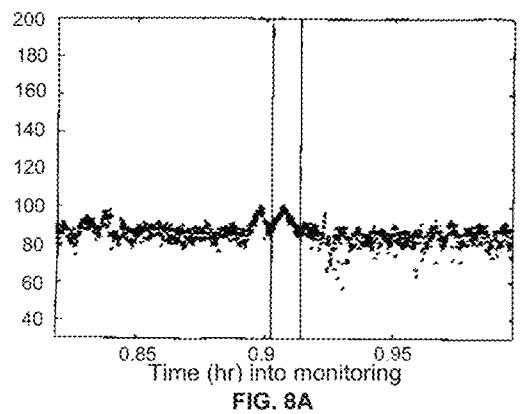
FIG. 8A shows a graph of heart rate vs. time, with epileptic events identified by ECoG indicated by vertical lines, from which an "M" pattern is discernible, in accordance with an illustrative embodiment of the present invention.
Figure 8B:
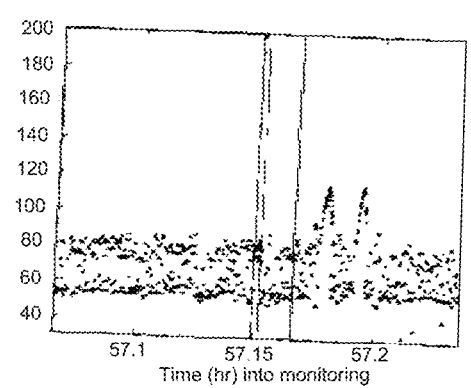
FIG. 8B shows a graph of heart rate vs. time, with epileptic events identified by ECoG indicated by vertical lines, from which an "M" pattern is discernible, in accordance with an illustrative embodiment of the present invention.

An exemplary state change template can be derived from the pattern shown in FIGS. 8A-8B, wherein the changes in heart rate during a seizure form a readily discernible "M" between 0.88 hr and 0.92 hr, having one positive phase relative to a reference heart rate parameter (calculated as the median value from about 0.85 hr to 0.89 hr and from about 0.93 hr to about 1.00 hr), three extrema (two maxima and one minimum, each being an extremum relative to about 20 seconds before and 20 seconds after), and four directions of heart rate change.

The state change template may be the "raw" pattern (analog or digitized) or it can be derived by smoothing, averaging, or otherwise mathematically processing sub-series of cardiac data obtained during state changes. A "matched filter" is a type of filter matched to the known or assumed characteristics of a target signal, to optimize the detection of that signal in the presence of noise. A matched filter is the filter with impulse response equal to the time reversed, complex conjugate impulse response of the input.

One skilled in the art will appreciate that when applying matched filter techniques to attempt to detect a pattern in a signal, the raw signal may first be transformed so that it has zero mean on a timescale of interest when the pattern is absent. Such transformation may include, but not be limited to, detrending or subtracting a background reference value (or time-varying reference signal) from the raw signal and is used to remove bias in the matched filter output and improve its signal-to-noise ratio.

Seizure detection may be performed over multiple time scales or window lengths listed in no particular order:

a) "Mesoscopic" corresponding to a scale of observation of several seconds to tens of seconds (e.g., 10-300 s) to capture at least in part, a change in the shape of heart rate plot representative of a state change.

b) "Microscopic" corresponding to the scale of observation of at least part of a heart beat such as that represented by an EKG's P-QRS-T complex.

c) "Macroscopic" corresponding to a scale of observation longer than 300 s to encompass more than the information contained in the mesoscopic scale or window as defined in a).

Seizure detection at a macroscopic scale provides information not obtainable with the two other scales (micro- and mesoscopic) allowing for the identification of certain patterns (defined herein as the occurrence of more than one triangle or parabola or combinations thereof within a macroscopic window).

A shape deformation (e.g., a deformed "M") may show local and global extrema that may be used for detection and validation purposes.

In one embodiment, the method comprises matched filtering. Matched filtering is a theoretical framework and not the name of a specific filter. A matched filter is a type of filter matched to the known or assumed characteristics of a target signal and is designed to optimize the detection of that signal in the presence of noise as it maximizes S/N. A matched filter's impulse response is equal to the time reversed, complex conjugate impulse response of the input.

The output response of a "matched" filter derived from meso-, micro- or macroscopic patterns, as it is passed through any of these patterns is characteristic (it forms a spatio-temporal pattern) and in turn may be used not only to validate detections but to allow detections before the convolution is completed ('early" detection).

A second filter matched to the first matched filter's output response may be run simultaneously with the first matched filter and its output response may be used for early detection and second level validation of the detection.

The pattern formed by any of the cardiac activity parameters may used as a matched filter. Other realizations such as the orthogonal and projected orthogonal matched filter detection (Eldar Y C. Oppenheim A, Egnor D. Signal Processing 2004; 84: 677-693), adaptive matched filter and parametric adaptive matched filter (Dong Y. Parametric adaptive filter and its modified version DSTO-RR-0313 My 2006 Australian Government, Dept. of Defence); the nearest matched filter for classification of spatio-temporal patterns (Hecht-Nielsen R. Applied Optics 1987; 26:1892-98), an outlier resistant matched filter (Gerlach K. IEEE Trans Aerospace Electronic Syst 2002; 38:885-901), a phase-only matched filter (Horner J L, Gianino P D. Applied Optics 1984; 23:812-16) may be also used for detection and validation of state changes such epileptic seizure.

The detection and validation of states based on the morphology or shape of signals may be performed at various time scales (micro-, meso-, or macroscopic) through estimation of the autocorrelation function of said shapes or patterns. Furthermore, estimation of the autocorrelation function of a reference state may also be used for detection and validation of state changes alone or in combination with the autocorrelation estimates of the state change shapes or patterns. Autocorrelation may be considered as an equivalent method to matched filtering.

Other methods, such as non-linear detectors (Theiler J, Foy B R, Fraser A M. Beyond the adaptive matched filter: Non-linear detectors for weak signals in high dimensional clutter. Proc SPIE 6565 (2007) 6565-02: 1-12) and maximum likelihood estimation (Forney G D, Maximum-likelihood estimation of digital sequences in the presence of intersymbol interference. IEEE Trans Information Theory 1972; 18:363-76), may be also applied in this invention.

Matching a heart rate shape to a state change template can be performed by any appropriate mathematical technique. For example, pattern matching by use of a matched filter is generally known to one skilled in the art. In one embodiment, the state change template comprises at least one matched filter. In one embodiment, a "match" refers to a match score found by a matched filter analysis of greater than about 0.75, such as greater than about 0.80, greater than about 0.85, greater than about 0.90, greater than about 0.95, greater than about 0.98, or greater than about 0.99. A "failure to match" refers to a match score found by a matched filter analysis of less than about 0.75, such as less than about 0.80, less than about 0.85, less than about 0.90, less than about 0.95, less than about 0.98, or less than about 0.99. However, these values may be changed as needed.

In one embodiment, the state change template comprises at least a state change matched filter and a reference parameter matched filter. A "match" can be defined as a match to the state change matched filter not accompanied by a match to the reference parameter filter.

Regardless of the type of filter, in one embodiment, the heart rate derivative shape has a matched filter score to said state change template greater than a value threshold for at least a duration threshold. For example, any of the values set forth above may be used as the value threshold and the duration threshold may be selected as any appropriate number of seconds or heart beats, such as 1 to 10 sec, or 1 to 10 beats, such as 3 beats.

In one embodiment, the state change template exists in a first timescale and said heart rate derivative shape is present in said first timescale. For example, the heart rate derivative shape is present over a first timescale not typically found in a reference heart rate derivative shape observed during rising from lying to sitting, rising from sitting to standing, minor physical exertion, exercise, or emotionally-intense experiences. This allows distinction between heart rate derivative shapes associated with a state change of interest, e.g., an epileptic seizure, and heart rate derivative shapes associated with normal daily activities.

In one embodiment, the state change template comprises at least one positive phase and at least one negative phase. In a further embodiment, the at least one positive phase is a period of elevated heart rate. In an even further embodiment, the period of elevated heart rate is a period of tachycardia. In people fifteen years of age and older, tachycardia is defined as a heart rate greater than 100 bpm. In another further embodiment, the at least one negative phase is a period of decreased heart rate. In an even further embodiment, the period of decreased heart rate is a period of bradycardia. Bradycardia is defined in adults as a heart rate less than 60 bpm.

In one embodiment, the state change template comprises at least two extrema of heart rate. In a further embodiment, the state change template can also comprise at least two phases.

The state change template may comprise one or more shapes readily discernible to the human eye. For example, the state change template may comprise a triangle, such as that shown in FIG. 6. Although in many cases, state change templates that appear more complex than a triangle may be useful, they can generally be understood as involving one or more triangles or parabolas and/or deformations thereof.

Figure 5:
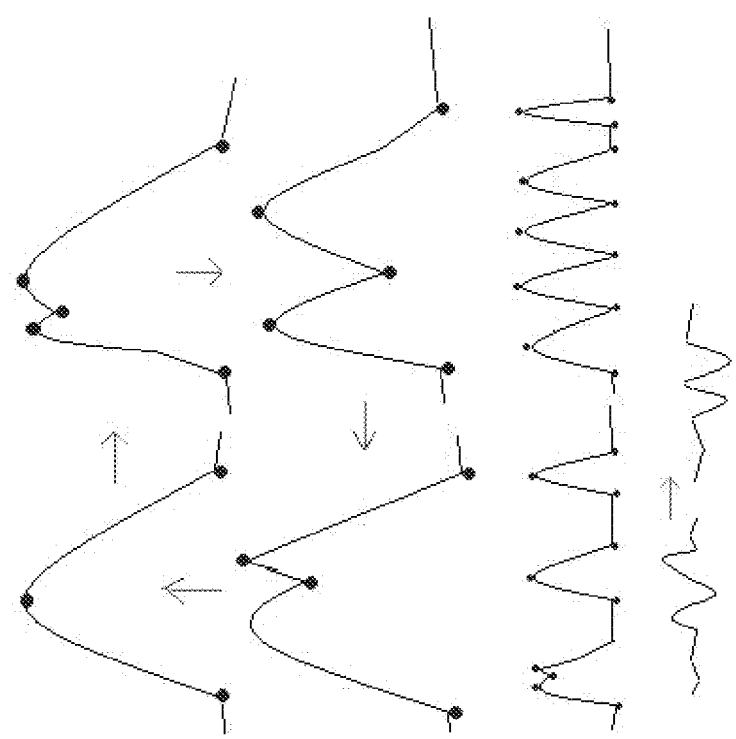
FIG. 5 shows basic shapes of a heart rate plot, from which more complex shapes can be produced by deformation in accordance with an illustrative embodiment of the present invention.

FIG. 5 illustrates the metamorphosis or transformation of circumictal heart rate shapes or patterns at a mesoscopic scale. The simplest shape is that of a parabola (left upper panel). In certain seizures a short-lived withdrawal or reduction of sympathetic influences or an increase in parasympathetic ones early in the course of a seizure causes a notch or indentation in the parabola (right upper panel). In other seizures (in the same subject or in a different subject), a later, more pronounced and prolonged withdrawal or reduction of sympathetic influences or an increase in parasympathetic ones (compared to that seen in the right upper panel) leads to a prominent indentation or notch (right lower panel), resembling the letter "M". A later, briefer, and less pronounced withdrawal or reduction of sympathetic influences or an increase in parasympathetic ones (compared to that seen in the right lower panel) causes an indentation in the parabola.

The relative balance of sympathetic and parasympathetic influences can be assayed at multiple timescales. As can be seen with reference to at least some of the figures discussed below, the relative balance of sympathetic and parasympathetic influences can oscillate on multiple timescales.

While a parabola is shown in FIG. 5 as an example, this may be replaced by a triangle or by any other topologically equivalent shape.

We have discovered a number of specific patterns or shapes occurring in at least some circumictal periods of at least some patients, which patterns or shapes may be used as the basis for a state change template as discussed herein.

Figure 6:
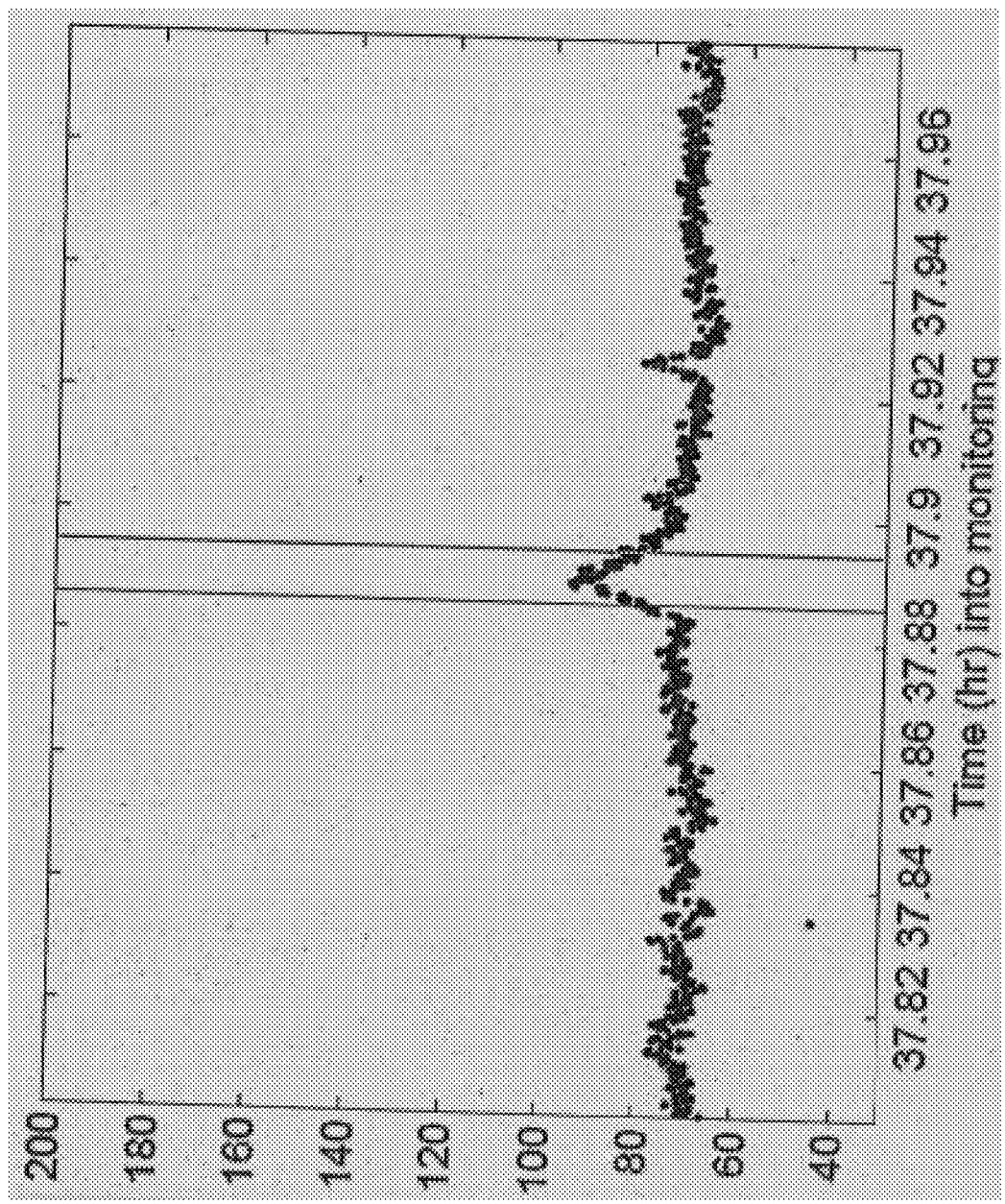
FIG. 6 shows a graph of heart rate (BPM) vs. time (hr), with an epileptic event identified by electrocorticography (ECoG) indicated by vertical lines, from which a triangle pattern is discernible, in accordance with an illustrative embodiment of the present invention.
Figure 7A:
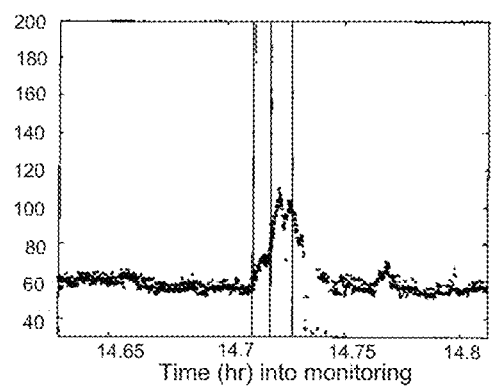
FIG. 7A shows a graph of heart rate vs. time, with epileptic events identified by ECoG indicated by vertical lines, from each of which a notched triangle pattern is discernible, in accordance with an illustrative embodiment of the present invention.
Figure 7B:
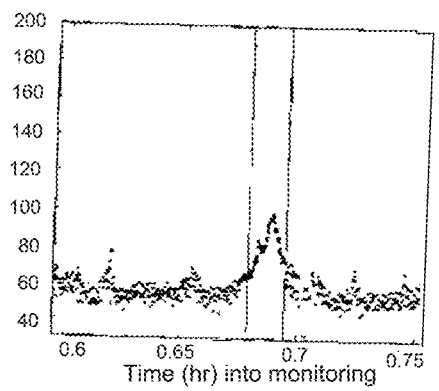
FIG. 7B shows a graph of heart rate vs. time, with epileptic events identified by ECoG indicated by vertical lines, from each of which a notched triangle pattern is discernible, in accordance with an illustrative embodiment of the present invention.
Figure 7C:
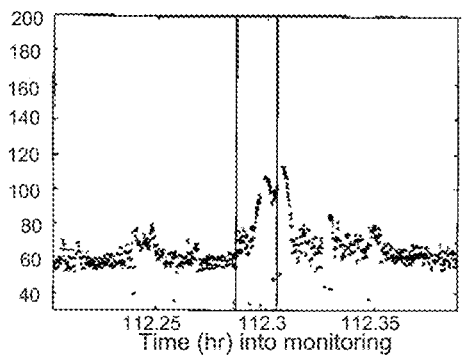
FIG. 7C shows a graph of heart rate vs. time, with epileptic events identified by ECoG indicated by vertical lines, from each of which a notched triangle pattern is discernible, in accordance with an illustrative embodiment of the present invention.
Figure 8C:
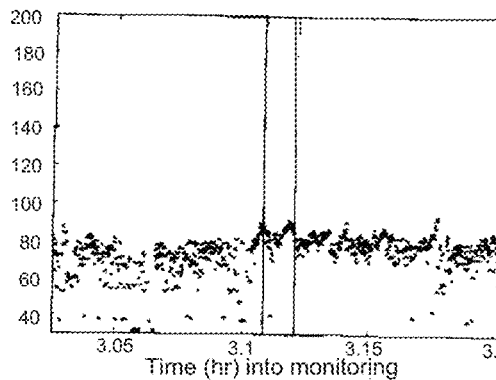
FIG. 8C shows a graph of heart rate vs. time, with epileptic events identified by ECoG indicated by vertical lines, from which an "M" pattern is discernible, in accordance with an illustrative embodiment of the present invention.
Figure 9:
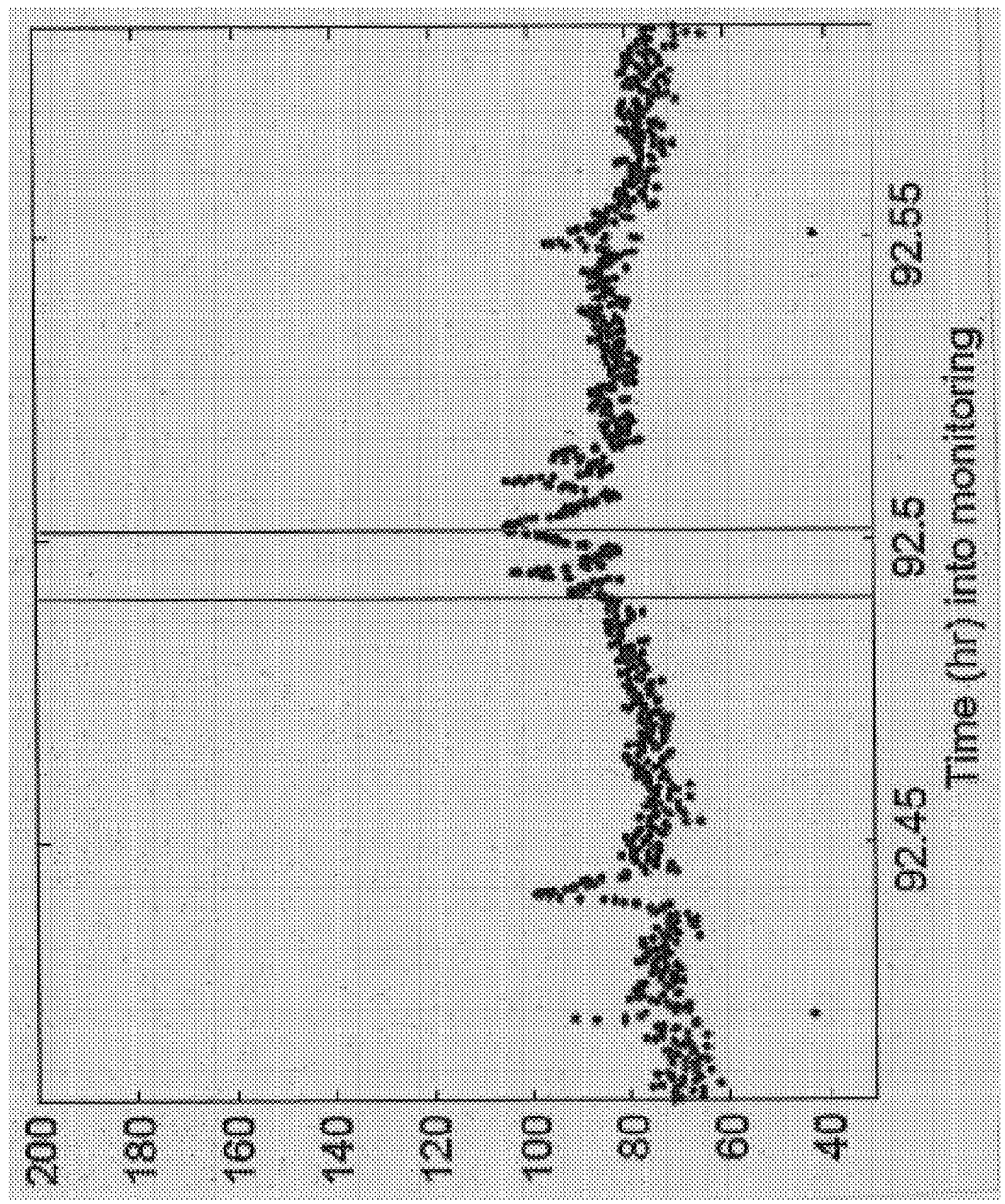
FIG. 9 shows a graph of heart rate vs. time, with an epileptic event identified by ECoG indicated by vertical lines, from which a "W" pattern is discernible, in accordance with an illustrative embodiment of the present invention.

Generally, the specific patterns or shapes can be considered as belonging to one of three categories:

Simple patterns, including the parabola shown in FIG. 5 or the triangle shown in FIG. 6, among others;

Complex patterns, including the notched triangle pattern of FIGS. 7A-7C, the "M" pattern of FIGS. 8A-8C, and the "W" pattern of FIG. 9, among others;

Polymorphic patterns, containing two or more simple and/or complex patterns, including fused simple and/or complex patterns, periodic or quasiperiodic oscillations, periodic or quasiperiodic oscillations overlaid on a longer term simple and/or complex patterns, and multiple simple and/or complex patterns, such as those shown in FIGS. 10-17B, among others.

Exemplary patterns or shapes are shown in FIGS. 6-17B. In each of these figures, a relevant portion of a graph of a patient's heart rate in beats per minute (BPM) vs. time in hours from the onset of ECoG monitoring of his or her seizure activity is shown. Vertical lines mark the electrographic onset and electrographic termination of a seizure.

The reader will have noticed that some patterns notable in FIGS. 6-17B as being closely correlated in time with a seizure also occur at times when no seizure was detected by ECoG. It should be pointed out that since monitoring of brain activity with intracranial electrodes is limited to certain regions, seizures may occur and go undetected if they originate in regions not monitored by the available electrodes. This may explain the presence of multiple heart rate patterns in the circumictal period when only one seizure was recorded. In other words, the cardiac data may indicate the occurrence of seizures that intracranial electrodes failed to detect. The use of cardiac information, such as the uses described and claimed herein, may supplement the inherent limitations of brain-based seizure detection.

FIG. 6 shows what may be termed a simple pattern, viz., a triangle, in accordance with an illustrative embodiment of the present invention. Herein, when discussing shapes, the words "triangle" and "parabola" can be used interchangeably. Generally, "triangle" will be used for convenience only.

FIG. 7A-C shows three graphs of what may be termed a notched triangle.

In various examples, the state change template may comprise one or more shapes that can be considered as comprising a plurality of triangles. For example, the state change template may comprise one or more shapes resembling letters of the Latin alphabet.

FIGS. 8A-C shows three graphs of what may be termed an "M" pattern, formed by two contiguous triangles or parabolae. The "M" pattern may be monophasic (the heart rate does not drop below the reference value or baseline) or multiphasic (after raising above the reference value, the heart rate drops below it). An "M" can be considered as distinct from a "notched triangle" in that the indentation of the M generally returns substantially to a baseline value and generally divides the M into substantially symmetrical halves.

The "M" patterns shown in FIGS. 8A-8C have total durations of about 60-90 sec, beginning anywhere from about 15 sec before electrographic onset to about 90 sec after electrographic onset. However, other total durations and beginning times relative to electrographic onset may occur in other "M" patterns.

FIG. 9 shows a graph of what may be termed a "W" pattern, discernible from about 15 sec after electrographic onset to about 20 sec after electrographic termination. Though not to be bound by theory, the "W" pattern may reflect differences (compared to the "M" pattern) in the timing of changes in autonomic influences during seizures.

The triangle, notched triangle, "M," and "W" patterns of FIGS. 6-9 can be considered to occur on a mesoscopic timescale. However, the same patterns may be discerned at shorter or longer timescales.

FIGS. 10-17B show patterns that can be considered to occur at long mesoscopic and/or macroscopic timescales. As can be seen and will be discussed below, the patterns of FIGS. 10-17B can generally be considered as polymorphic patterns comprising two or more of the basic shapes, simple patterns, or complex patterns discussed above.

Figure 10:
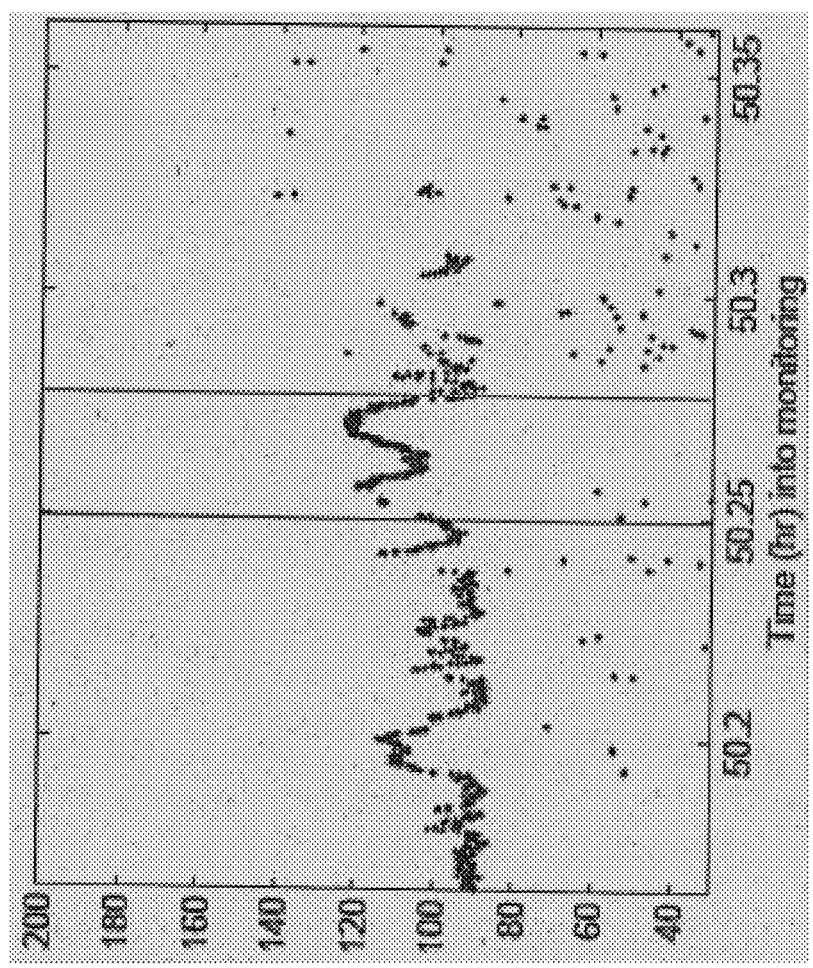
FIG. 10 shows a graph of heart rate vs. time, with an epileptic event identified by ECoG indicated by vertical lines, from which a fused "M" and "W" pattern is discernible, in accordance with an illustrative embodiment of the present invention.

FIG. 10 shows a fused "M" and "W" pattern. The "W" can be considered as starting at about 30 sec before electrographic onset and ending at about 60-75 sec after electrographic onset in the region of highest heart rate during the seizure event. The "M" can be considered as starting a few seconds before electrographic onset and ending about at electrographic termination. One may also discern a "W" occurring at a microscopic or short mesoscopic timescale at the notch of the "M."

Alternatively or in addition, a person of ordinary skill in the art, having the benefit of the present disclosure, may discern an "M" beginning at about 45-60 sec before electrographic onset and ending at about the middle of the seizure, with a "W" beginning about 30 sec after electrographic onset and ending about 15-30 sec after electrographic termination.

Figure 11A:
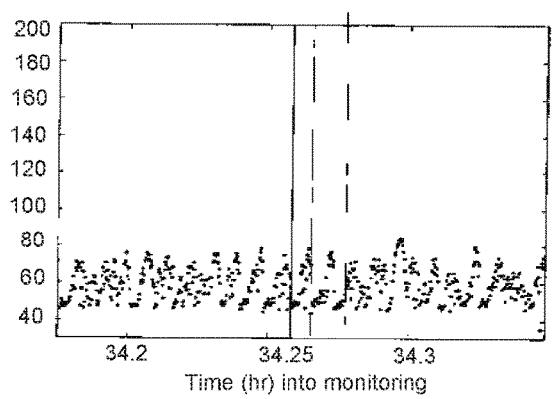
FIG. 11A shows a graph of heart rate vs. time, with epileptic events identified by ECoG indicated by vertical lines, from which a pattern of periodic oscillations is discernible, in accordance with an illustrative embodiment of the present invention.
Figure 11B:
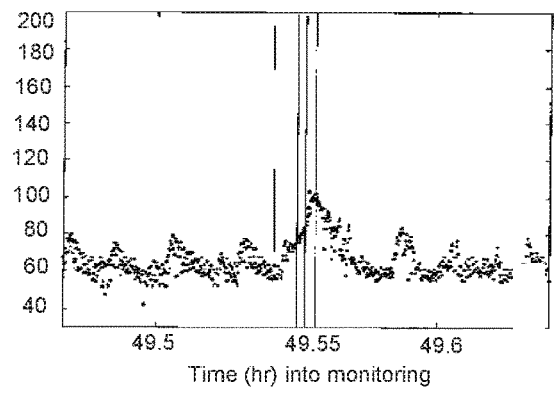
FIG. 11B shows a graph of heart rate vs. time, with epileptic events identified by ECoG indicated by vertical lines, from which a pattern of periodic oscillations is discernible, in accordance with an illustrative embodiment of the present invention.

FIGS. 11A-B shows two graphs of patterns of periodic or quasiperiodic oscillations. (For convenience, we will use the term "periodic," although it must be borne in mind that the frequency and the amplitude of the oscillations associated with a single seizure in one patient may vary over the course of about 10 min, as shown in FIGS. 11A-B. In other words, the term "periodic" is not limited herein to refer to series of oscillations with fixed frequency and amplitude).

The pattern of periodic oscillations may be deformed by a seizure event (e.g., FIG. 11B). In instances where this is not the case, a dysfunction of the patient's autonomic nervous system may be indicated. For example, FIG. 11A shows a rapid oscillation of the patient's heart rate by as much as 40 BPM in a short time.

Detecting a pattern in a preictal period in a time series of heart rate data may be considered, at least in some patients, as a "prediction" of a seizure and/or an indication of a period of greater risk of a seizure. Alternatively or in addition, it may be used to aid detection of seizures originating in brain regions not surveyed by intracranial electrodes.

Figure 12:
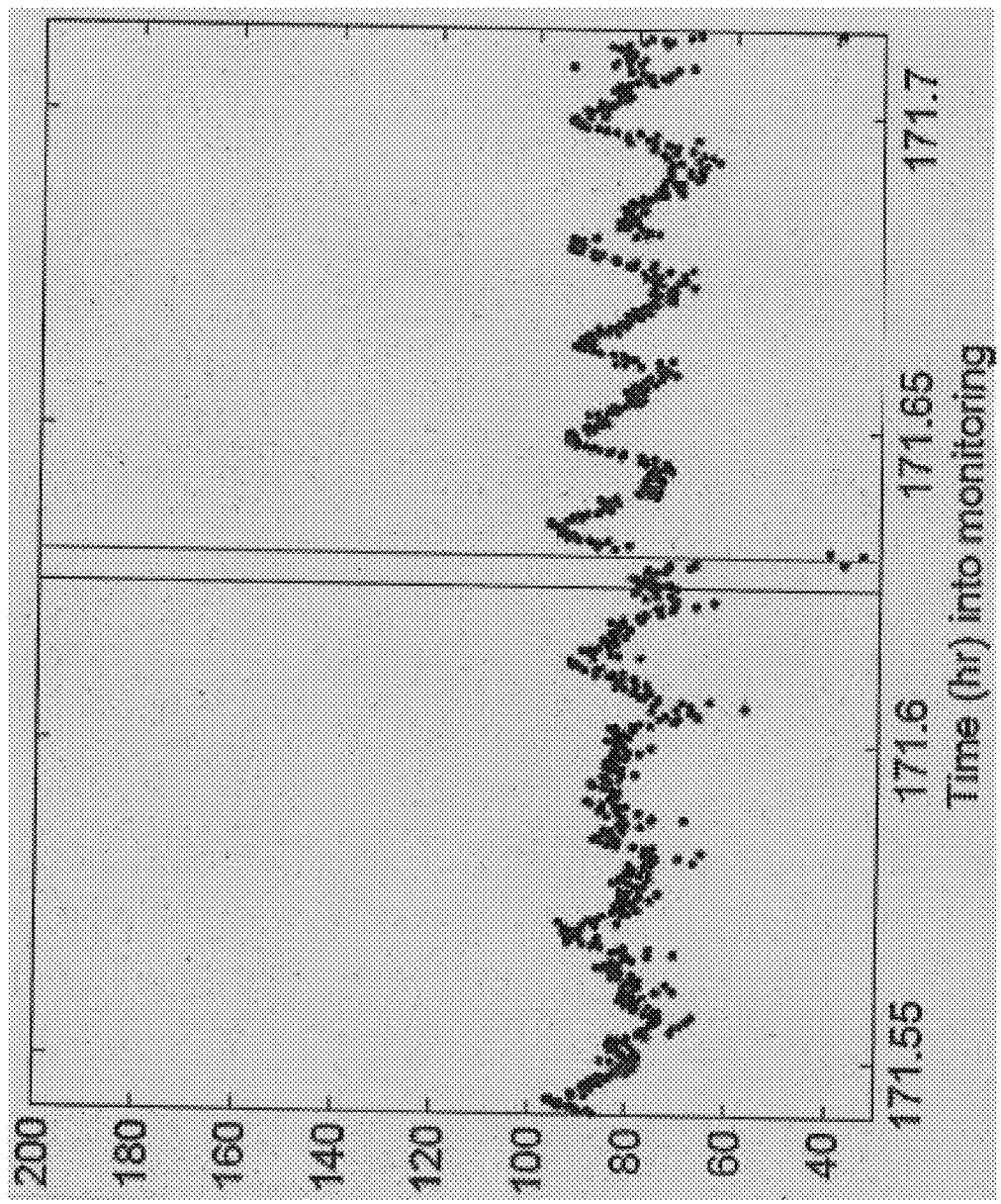
FIG. 12 shows a graph of heart rate vs. time, with an epileptic event identified by ECoG indicated by vertical lines, from which a pattern of periodic oscillations, specifically forming a sawtooth pattern, is discernible, in accordance with an illustrative embodiment of the present invention.

Multiple triangles with a certain degree of periodicity and either monophasic or biphasic nature can form what may be viewed as a "sawtooth" pattern in the circumictal period. FIG. 12 shows a graph of another pattern of periodic oscillations. The periodic oscillations from about 15-30 sec after the seizure to about 3 min after the seizure can be considered a sawtooth pattern.

Figure 13A:
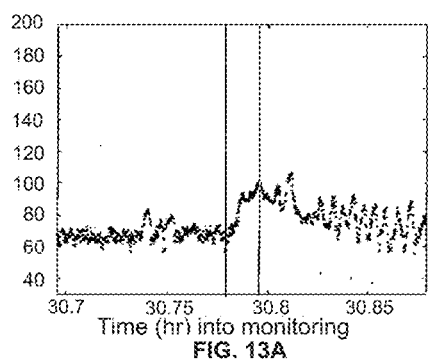
FIG. 13A shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present invention.
Figure 13B:
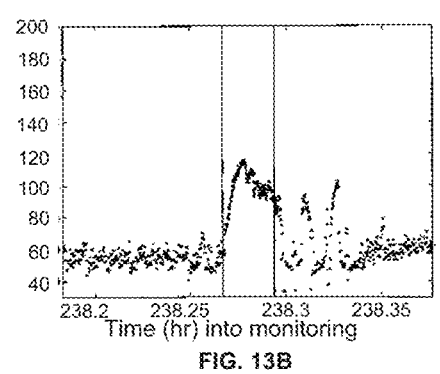
FIG. 13B shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present invention.
Figure 13C:
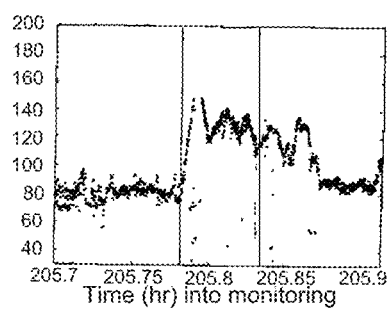
FIG. 13C shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present invention.
Figure 13D:
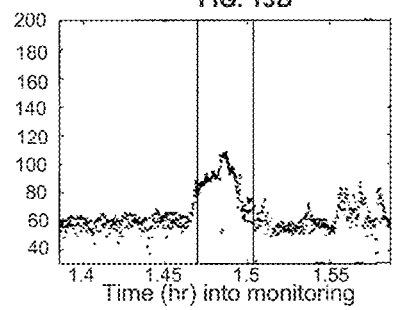
FIG. 13D shows a graph of heart rate vs. time, with epileptic events identified by ECoG indicated by vertical lines, from which a pattern of periodic oscillations overlaid on a longer-timescale triangle pattern is discernible, in accordance with an illustrative embodiment of the present invention.

FIGS. 13A-D shows four graphs of patterns of periodic oscillations overlaid on a longer-timescale triangle pattern. For example, the pattern in FIG. 13A shows an asymmetric triangle with a trailing slope lasting about 5 min, on which is overlaid a pattern of periodic oscillations having an average wavelength of about 20 sec is discernible from about 90 sec after the seizure until the end of the window shown.

Figure 14:
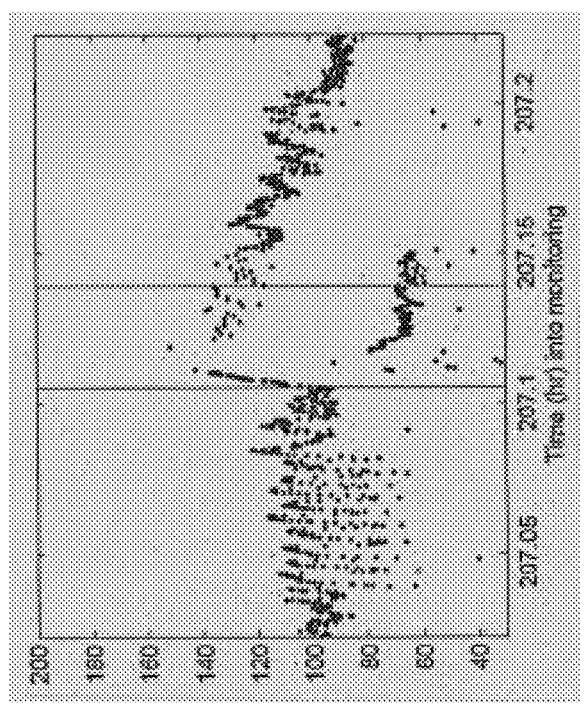
FIG. 14 shows a graph of heart rate vs. time, with an epileptic event identified by ECoG indicated by vertical lines, from which periodic oscillations forming a "comb" pattern are discernible, as well as a pattern of lower amplitude periodic oscillations overlaid on a longer-timescale triangle pattern is discernible, in accordance with an illustrative embodiment of the present invention.

FIG. 14 shows, in addition to a pattern of periodic oscillations overlaid in the post-ictal period on a longer-timescale triangle pattern, a comb pattern in the preictal period. For a duration of about 2.5 min starting about 3.5 min before electrographic onset, a pattern of periodic oscillations is shown with pronounced negative amplitudes (relative to the average heart rate over the first 30-45 sec of the window) and an average wavelength of about 15 sec. Again, detecting a pattern in a preictal period in a time series of heart rate data may be considered, at least in some patients, as a "prediction" of a seizure and/or an indication of a period of greater risk of a seizure. Alternatively or additionally, the presence of one pattern of long duration or more than one pattern of any duration in the circumictal period, are indicative of cardiac or autonomic instability. This information may be used to warn the patient or his caregiver(s) of an increased risk of a serious outcome and/or institute therapeutic measures.

Figure 15:
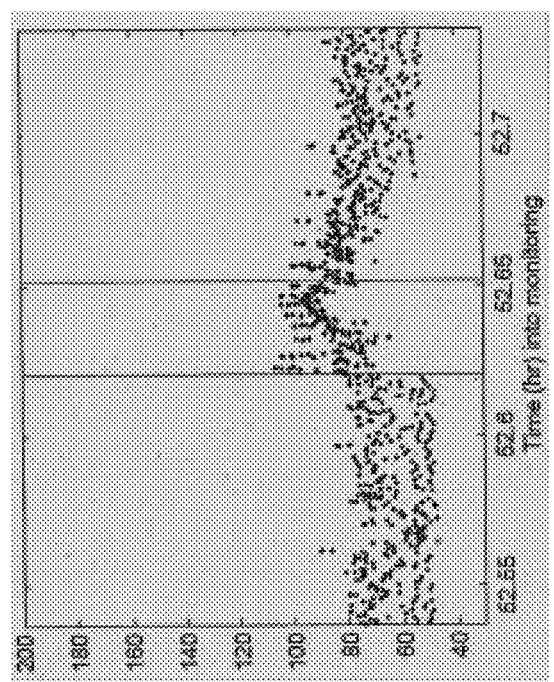
FIG. 15 shows a graph of heart rate vs. time, with an epileptic event identified by ECoG indicated by vertical lines, from which a pattern of periodic oscillations overlaid on a longer-timescale parabola pattern is discernible, in accordance with an illustrative embodiment of the present invention.

FIG. 15 shows another comb pattern, this one with pronounced positive amplitudes, overlaid on a longer-timescale parabola.

Figure 16:
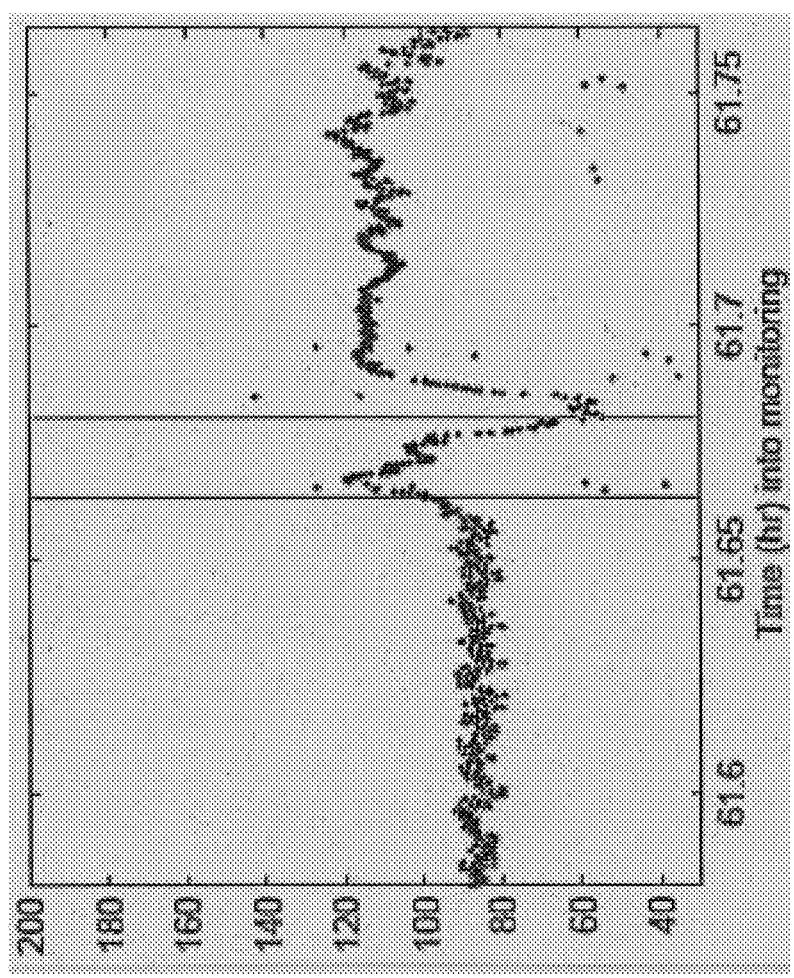
FIG. 16 shows a graph of heart rate vs. time, with an epileptic event identified by ECoG indicated by vertical lines, from which a triphasic pattern is discernible, in accordance with an illustrative embodiment of the present invention.

FIG. 16 shows a triphasic pattern relative to the preictal baseline, in which a first positive phase forms a notched triangle from just before electrographic onset until late in the seizure; a second, negative phase follows until about 30-45 sec after the seizure; and a third, positive phase ensues with a duration of about 4 min until the end of the window.

Figure 17A:
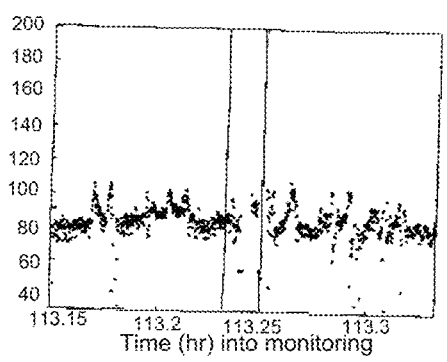
FIG. 17A shows a graph of heart rate vs. time, with epileptic events identified by ECoG indicated by vertical lines, from which multiple "M" and/or "W" patterns are discernible, in accordance with an illustrative embodiment of the present invention.
Figure 17B:
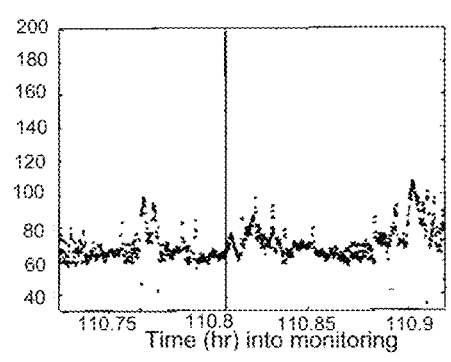
FIG. 17B shows a graph of heart rate vs. time, with epileptic events identified by ECoG indicated by vertical lines, from which multiple "M" and/or "W" patterns are discernible, in accordance with an illustrative embodiment of the present invention.

FIGS. 17A-B shows two graphs from which multiple "M" and/or "W" patterns are discernible in all three of the preictal, ictal, and postictal time periods. These multiple "M" and/or "W" patterns can be considered as part of a macroscopic pattern comprising a plurality of complex shapes.

In addition, very rapid oscillations in heart rate may also occur, and along with lower frequency oscillations, may provide useful insight into the behavior of heart rate variability circum-ictally and of its usefulness for seziure detection, given its differences from those observed outside the circum-ictal period. That is, oscillations at two frequencies (e.g., slow and fast) or more than two frequencies (e.g., very fast, slow, and very slow) may overlap to form a pattern that is commonly associated with a circumictal period.

Any one or more of the patterns shown in FIGS. 6-17B, among others, can be taken as the basis for a state change template. Also, HRV values can be derived from the time series of heart rates depicted in FIGS. 6-17B, and one or more distinctive patterns discernible from the HRV values can be used as the basis for a state change template. Such distinctive patterns would generally be expected to be distinct from HRV changes resulting from exercise or normal exertion.

Regardless of how HRV values are determined, in one embodiment, the pattern or shape of heart rate variability (as distinct from heart rate) measured at any or all of the timescales (micro-, meso-, or macroscopic) may be used as a template for detection and quantification of state changes using matched filtering or its autocorrelation function.

In a particular embodiment, the state change template comprises one phase relative to the reference heart rate parameter, three extrema, four directions of heart rate change, and two periods of increased heart rate relative to the reference heart rate parameter. This state change template may be considered to be the "M" pattern shown in FIGS. 8A-8C.

Multiple state change templates, including but not limited to multiple templates at different timescales, may be used for various purposes. For example, a first template found to have a particularly high sensitivity, specificity, or both can be used as a primary detection technique, with other templates used to validate detections made by the first template. For another example, a template found to have high sensitivity but low specificity (i.e., giving detections with a relatively high false positive rate) can be paired with another template found to have high specificity to be used in detections with higher sensitivity and specificity than either alone. For still another example, a first template can be used to identify a state change e.g., from a non-circumictal state to a preictal state, and this identification can be used to trigger use of a second template to identify a second state change, e.g., from a preictal state to an ictal state. For a particular example, a comb pattern can be used to identify a state change from a non-circumictal state to a preictal state, and an "M" pattern can be used to identify a state change from a preictal state to an ictal state.

In one embodiment, a plurality of matched filters (and/or the output of one or more of the matched filters as another matched filter or filters) can be used. For example, two or three matched filters, each on a separate one of the macroscopic, mesoscopic, and microscopic timescales can be run simultaneously on the time series of heart rate derivative data. After adequate analysis, comparisons of the results of matched filtering at the three times scales can be made to find the matched filter/timescale combination(s) giving highest sensitivity, highest specificity, fastest detection, or two or more thereof. Depending on the intended use, the most useful matched filter/timescale can then be used and run continuously and its output (detection) used to run the other matched filters/timescales for detection of changes (at longer or shorter time scales) and validation of detected changes.

Alternatively or in addition to the state change detections discussed herein, circumictal changes at various times scales may be used for assessment of disease state, both among circumictal changes monitored over long time periods (such as months or years) and between circumictal and non-circumictal states. In one embodiment, such disease state assessment may include assessment of the patient's risk of epilepsy-related sudden death (SUDEP).

Regardless of the desired use of circumictal data, circumictal changes may be quantified in one or more dimensions. In one embodiment, the output value of a detection, a disease state assessment, or the like can be monitored as a function of time (days, month years), both inter-circumictally and circumictally vs. non-circumictally, with the results analyzed for the presence of changes and trends. In another embodiment, circumictal changes can be classified as a function of pattern type (e.g., simple, complex, or polymorphic) and their temporal evolution tracked. In another embodiment, the temporal density of the circumictal period can be defined as percent time spent in a pattern(s).

Quantification of the match between the heart rate derivative shape and the state change template can also provide information about the duration of a seizure. In one embodiment, the method further comprises indicating the termination of the state change based upon a determination that the heart rate derivative shape fails to match the state change template, after an indication of an occurrence of a state change.

In one embodiment, the state change template further comprises at least one second characteristic selected from a magnitude of heart rate change relative to the reference heart rate parameter, a slope of heart rate change, a duration of one or more phases, a duration from a heart rate excursion from the reference heart rate parameter to a peak or a trough heart rate, a total duration of all the phases, or a duration of a constant slope of heart rate change; and indicating an occurrence of a state change is based upon a determination that the heart rate shape matches a state change template in both the at least one characteristic and in the at least one second characteristic.

The slope can be measured on any time scale, though for cardiac data, it may be smoother if taken over multiple beats, such as five or fifteen beats, or over a length of time, such as five to fifteen seconds. The term "constant slope" is used herein to refer to a fit, such as a least-squares fit or other fit, of the data series in question that has a sufficiently high fit to a straight line as to commend itself to the person of ordinary skill in the art as being a constant. For example, a region of a data series having a linear least-squares fit with an $R^2$ value of at least 0.9 can be considered to have a constant slope.

As stated above, a state change can be indicated by quantifying the match of the heart rate shape to the state change template. This state change indication can be considered as the sole indication of a state change, it can be validated by other techniques of state change identification, or it can be used to verify state changes indicated by other techniques. Such other techniques include those described elsewhere herein, as well as others known to the person of ordinary skill in the art or others the subject of one or more patent applications, such as U.S. patent application Ser. No. 12/770,562, filed Apr. 29, 2010; Ser. No. 12/771,727, filed Apr. 30, 2010; and Ser. No. 12/771,783, filed Apr. 30, 2010.

In one embodiment, the determination comprises using a first matched filter to yield a first output, building a second matched filter from the first output, and using the second matched filter to detect the state change. In other words, because the passage of a first matched filter over a data window will produce a stereotypical output when it begins passing over a shape which it matches, the stereotypical output itself can be used to detect a state change prior to, or as a validation of, a detection by the first matched filter.

Thus, in one embodiment, the method further comprises identifying an occurrence of a state change; and wherein said determining said heart rate derivative shape and said indicating are performed in response to said identifying, to validate said identifying.

In another embodiment, the method further comprises identifying an occurrence of a state change in response to said indicating, to validate said indicating. In a further embodiment, the method further comprises obtaining data relating to at least a portion of a heart beat complex from said patient; comparing said at least said portion of said heart beat complex with a corresponding portion of a reference heart beat complex template of said patient, wherein the reference heart beat complex template is not indicative of a state change; and validating said indicating an occurrence of a state change, wherein said validating is based upon a determination that said heart beat complex fails to match said reference heart beat complex template.

In one embodiment, the reference heart beat complex template is selected from a normal template (e.g., a reference heart beat complex template not indicative of a state change from a patient with healthy heart activity) or an abnormal template (e.g., a reference heart beat complex template not indicative of a state change from a patient with current or past unhealthy heart activity).

For example, a heart rate derivative shape present over a first timescale not typically found in a reference heart rate derivative shape observed during rising from lying to sitting, rising from sitting to standing, minor physical exertion, exercise, or emotionally-intense experiences can be used to indirectly validate an identification of a seizure made from a rise in heart rate, or vice versa.

Alternatively or in addition, in another embodiment, the method comprises determining a second reference heart rate parameter; determining a second heart rate derivative shape from said time series of cardiac data, wherein said second heart rate derivative shape comprises at least one second characteristic selected from a number of phases relative to said reference heart rate parameter, a number of positive phases relative to said reference heart rate parameter, a number of negative phases relative to said reference heart rate parameter, a number of extrema of said second heart rate derivative, or a number of directions of change of said second heart rate derivative; and validating said indicating an occurrence of a state change, wherein said validating is based upon a determination that said second heart rate derivative shape matches a second state change template in said at least one second characteristic.

The present invention also provides a method for indicating an occurrence of a state change, comprising obtaining data relating to at least a portion of a heart beat complex from a patient; comparing the at least the portion of the heart beat complex with a corresponding portion of a reference heart beat complex template of the patient; and indicating an occurrence of a state change based upon a determination that the heart beat complex fails to match the reference heart beat complex template.

A heart beat complex is used herein to refer to a PQRST complex, as is known from the electrocardiography (EKG) art, from a single heart beat, including both the relative and absolute magnitudes of the P-, Q-, R-, S-, and T-waves, and all of the intervals P-Q, P-R, P-S, P-T, Q-R, Q-S, Q-T, R-S, R-T, and S-T. A portion of the heart beat complex is then any one or more of the relative and/or absolute magnitudes of the waves, their shapes, and/or one or more of the intervals between waves. A relative magnitude may be defined according to any one or more of the waves of the complex, e.g., an R-wave amplitude can be defined as r times the P-wave amplitude. FIG. 18 shows exemplary heart beat complexes with P- and R-waves identified by name. The horizontal lines are drawn for convenience, to point out plausible deviations between the various waves of different beat complex.

Although the term "a heart beat complex" is used above, a plurality, such as, but not necessarily, a sequential plurality, of heart beat complexes can be used, with the comparing being done for one or more of the plurality of heart beat complexes. The plurality may be a fixed set of beats or a moving window over a predetermined time or number of beats.

In one embodiment, the portion of the heart beat complex comprises at least one of an amplitude of a P wave, a polarity of a P wave, at least one of an amplitude of an R wave, a polarity of a Q wave, a polarity of an R wave, an amplitude of an S wave, a polarity of an S wave a polarity of an S wave, an amplitude of a T wave, a polarity of a T wave, an area under the curve of a P wave, an area under the curve of a Q wave, an area under the curve of an R wave, an area under the curve of an S wave, an area under the curve of a T wave, a width of a P wave, a with of a Q wave, a width of an n R wave, a width of an S wave, a width of a T wave, a morphology of a P wave, a morphology of a Q wave, a morphology of an R wave, a morphology of a T wave, a magnitude of a change in the distance from a P wave to a Q wave, a magnitude of a change in the distance from a P wave to an R wave, a magnitude of a change in the distance from a Q wave to an R wave. a magnitude of a change in the distance from an R wave to an S wave, a magnitude of a change in the distance from an R wave to a T wave, a magnitude of a change in the distance from an S wave to a T wave, a magnitude of an S-T segment elevation, a magnitude of an S-T segment depression, a magnitude of a Q-T segment elevation, a magnitude of a Q-T segment depression, a P-R interval, an R-S interval, an S-T interval, an R-T interval, and a Q-T interval.

The reference heart beat complex template can be derived from any non-state change heart beats. Such beats may be one, some, or all the same beats used to define the reference heart rate parameter and/or reference HRV described above, but need not be any of the same beats. In one embodiment, the reference heart beat complex template comprises at least one matched filter. In a further embodiment, the heart beat complex fails to match the reference heart beat complex template if a matched filter score for the heart beat complex to the at least one matched filter is less than a heart beat complex value threshold.

Although one reference heart beat complex template is referred to above, a plurality of reference heart beat complexes may be used. For example, a plurality of reference heart beat complexes can be used on the same heart beats, or one or more of the plurality can be used at different times of day, under different states of exertion or arousal, in view of changes in heart health histories or differences in heart health between patients, among other possibilities. In one embodiment, a second reference heart beat complex template comprises at least one of T wave depression, P-Q segment elongation, another abnormality, or two or more thereof, relative to the canonical "normal" heart beat complex.

Alternatively, one or more heart beat complex templates derived from heart beat complexes observed during one or more periods of state change may be used, with a state change declared if the heart beat complex(es) match(es) the state change heart beat complex template(s).

Figure 19:
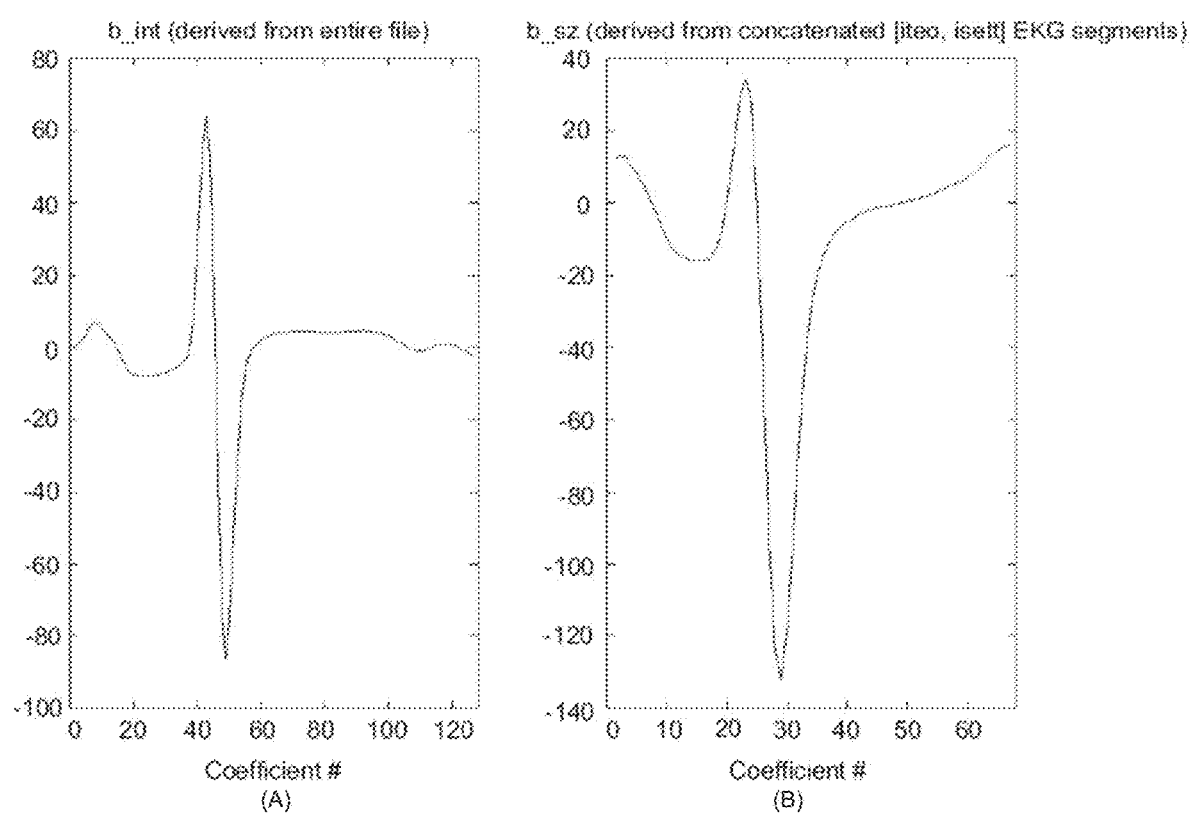
FIG. 19 shows a first heart beat complex derived from data collected over an entire period of EKG monitoring of a patient (A) and a second heart beat complex derived from EKG data collected from the same patient during circumictal periods only (B).

FIG. 19A shows an exemplary heart beat complex derived from data collected over an entire period of EKG monitoring of a patient, which may be used as a reference heart beat complex template. FIG. 19B shows an exemplary heart beat complex derived from EKG data collected from the same patient during circumictal periods only, which may be used as a state change heart beat complex template.

In the event a plurality of reference heart beat complex templates are used, one or more of the templates may be modified over time, based on observed changes in the patient's heart beat complexes, such as during non-state-change periods.

The at least portion of the heart beat complex and the corresponding portion of the reference heart beat complex template can be compared using any of the pattern matching techniques described herein. Because the reference heart beat complex template is taken from non-seizure heart beats, a failure to match between the at least portion of the heart beat complex and the corresponding portion of the reference heart beat complex template is an indirect indication of a seizure.

Quantification of the match between a portion of a heart beat complex and the corresponding portion of the reference heart beat complex template can also provide information about the duration of a seizure. In one embodiment, the method further comprises obtaining a time series of data relating to a plurality of heart beat complexes from the patient; comparing at least a portion of each of a sequential plurality of heart beat complexes with a corresponding portion of the first reference heart beat complex template; and indicating the termination of the state change based upon a determination that at least one heart beat complex of the sequential plurality matches the reference heart beat complex template, after an indication of an occurrence of a state change. Matched filters can be used in this determination, as described elsewhere herein.

In one embodiment, the determination further comprises analyzing one or more of a pulse shape, an R wave amplitude, an apex cardiogram, or a pressure wave, to validate or classify the state change.

In one embodiment, a heart beat complex fails to match a reference heart beat complex template if a matched filter output for said heart beat complex is less than a first matched filter threshold, or differs from a second matched filter threshold by at least a predetermined magnitude.

Also similarly to the heart rate derivatives described above, a state change can be indicated by quantifying the match of the portion of the heart beat complex to the reference heart beat complex template. This state change indication can be considered as the sole indication of a state change, it can be validated by other techniques of state change identification, or it can be used to verify state changes indicated by other techniques. Such other techniques include those described elsewhere herein, as well as others known to the person of ordinary skill in the art or others the subject of one or more patent applications, such as U.S. patent application Ser. No. 12/770,562, filed Apr. 29, 2010; Ser. No. 12/771,727, filed Apr. 30, 2010; and Ser. No. 12/771,783, filed Apr. 30, 2010.

Thus, in one embodiment, the method further comprises identifying an occurrence of a state change; wherein the obtaining, the comparing, and the indicating are performed in response to the identifying, to validate the identifying.

Particularly, the prior indicating can be performed using heart rate or HRV data, and in one embodiment, one or more heart beats taken from the reference heart rate parameter of the heart rate or HRV data can be used to define the reference heart beat complex template and one or more heart beats taken from the excursion of the heart rate or HRV data from its reference heart rate parameter can be used to as the heart beat complex from which a portion is matched with a corresponding portion from the reference heart beat complex template. By "zooming" from the heart rate or HRV shape into one or more individual heart beats giving rise to the heart rate or HRV shape, a state change indication from HRV data can be validated. For example, if the heart rate or HRV shape gives an indication of a state change, but one or more heart beat complexes from the putative state change match the reference heart beat complex template, the excursion of heart rate or HRV from the reference heart rate parameter may be considered to result from exercise or another non-seizure-event source.

In another embodiment, the method further comprises identifying an occurrence of a state change in response to said indicating, to validate said indicating. For example, identifying an occurrence of a state change to validate an indication can be performed by using a prior detection algorithm, using a second characteristic of the state change template, or matching at least a portion of a heart beat complex with a corresponding portion from a reference heart beat complex template, among other techniques.

The present invention also provides a method for identifying a state change template from cardiac data, comprising obtaining a time series of cardiac data from a patient during a first time window; determining a time of occurrence of at least one state change suffered by the patient during the first time window; and either (i) determining at least one state change template in the time series of cardiac data within the first time window and timewise correlated with the at least one state change, wherein the at least one state change template comprises at least one characteristic selected from a number of phases relative to a reference heart rate parameter, a number of extrema, a number of directions of change, a number of positive phases relative to said reference heart rate parameter, or a number of negative phases relative to said reference heart rate parameter, or (ii) determining at least one reference heart beat complex template in the time series of cardiac data within the first time window and not timewise correlated with the at least one state change.

In a particular embodiment, the at least one characteristic comprises at least one of the amplitude of at least one phase, the duration of at least one phase, the valence (positive or negative) of at least one phase, at least one slope of at least one phase, the arc length of at least one phase, the number of extrema in at least one phase, and the sharpness of the extrema of at least one phase.

The cardiac data can comprise one or more of heart rate data, HRV data, or heart beat complex data, such as data from at least a portion of each of a plurality of heart beat complexes, among others. The cardiac data can be derived from signals collected from or related to EKG, heart sounds (such as can be collected by a microphone mounted on the skin of the chest), blood pressure, apex cardiography, echocardiography, thermography, or blood flow velocities estimated by Doppler imaging, among other techniques known to the person of ordinary skill in the art.

The time of occurrence of the at least one state change can be determined by any appropriate technique, such as EEG, cardiac-based seizure detection (such as that disclosed in U.S. patent application Ser. No. 12/770,562, filed Apr. 29, 2010; Ser. No. 12/771,727, filed Apr. 30, 2010; and Ser. No. 12/771,783, filed Apr. 30, 2010), testing of the patient's responsiveness (such as that disclosed in U.S. patent application Ser. No. 12/756,065, filed Apr. 7, 2010, the disclosure of which is hereby incorporated herein by reference), among other techniques known to the person of ordinary skill in the art or otherwise available.

The finding of a timewise correlation of at least one state change template with a state change, or the finding of a non-timewise correlation of at least one reference heart beat complex template with a state change, can be performed by any appropriate technique. "Timewise correlation" refers to any substantially repeated duration between a putative template and a state change, and includes putative templates taking place before a state change, during a state change, or after a state change.

The state change template can be further defined according to at least one second characteristic selected from a magnitude of cardiac data value change relative to the reference heart rate parameter cardiac data series, a slope of cardiac data value change, a duration of one or more phases, a duration from a cardiac data excursion from the reference heart rate parameter cardiac data series to a peak or a trough cardiac data series, a total duration of a cardiac data excursion from the reference heart rate parameter cardiac data series, or a duration of a constant slope of cardiac data series change.

In another embodiment, the present invention relates to a method for determining at least one property of a pattern indicative of an occurrence of a state change. In one embodiment, this method comprises obtaining a time series of cardiac data from a patient; determining if at least one heart rate derivative shape forms at least one pattern; and determining at least one property of the pattern.

For example, in one embodiment, the at least one property of the pattern comprises a shape of the pattern, a time of occurrence of the pattern, a time elapsed between occurrences of the pattern, and an association of the pattern with a state change of a body organ.

Any state change of any body organ may be considered. In one embodiment, the at least one property of the pattern is an association of the pattern with a state change of the brain. In a further embodiment, the state change of the brain is an epileptic seizure.

The state change template or reference heart beat complex template produced by the present method can be used in a method as described above.

However the state change is identified, and regardless of the state change template, the timescale, and the subperiod of the circumictal period in which state changes are detected, in some embodiments, an indication of a state change can be used as the basis for taking a responsive action selected from warning, logging the time of a state change, computing and storing one or more state change severity indices, treating the state change, or two or more thereof. In one embodiment, quantification of one or more state change severity indices can be performed through comparisons of matched filtering outputs, although scaling and/or other appropriate transformation may be required when the shapes are similar but their sizes are not.

A state change warning may be given as, for example, a warning tone or light, vibration, pressure, or scent implemented by a medical device or a device adapted to receive indications of the state change; as an automated email, text message, telephone call, or video message sent from a medical device or a unit in communication with a medical device to the patient's cellular telephone, PDA, computer, television, 911 or another emergency contact number for paramedic/EMT services, etc. Such a warning may allow the patient or his or her caregivers to take measures protective of patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

The time may be logged by receiving an indication of the current time and associating the indication of the current time with an indication of the state change.

State change severity indices may be calculated and stored by appropriate techniques and apparatus.

In an exemplary embodiment of the present invention, any method of indicating a seizure can further comprise taking a responsive action based upon the identifying the state change. The responsive action may include providing a warning and/or notifying the patient or a caregiver, logging the time of a state change, computing and storing one or more state change severity indices, or treating the state change.

In one embodiment of the present invention, treating the state change comprises providing a neurostimulation therapy. The neurostimulation therapy may involve applying an electrical, mechanical, magnetic, electro-magnetic, photonic, acoustic, cognitive, sensori-perceptual and/or chemical signal to a neural structure of the body. The neural structure may be a brain, a spinal cord, a peripheral nerve, a cranial nerve, or another neural structure. In a particular embodiment, the responsive action comprises treating the state change by providing a cranial nerve stimulation therapy. Cranial nerve stimulation has been proposed to treat a number of medical conditions pertaining to or mediated by one or more structures of the nervous system, including epilepsy, movement disorders, depression, anxiety disorders and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515.

In some embodiments, electrical neurostimulation may be provided by implanting an electrical device underneath the skin of a patient and delivering an electrical signal to a nerve such as a cranial nerve. In another alternative embodiment, the signal may be generated by an external pulse generator outside the patient's body, coupled by an RF or wireless link to an implanted electrode. In one embodiment, the treatment comprises at least one of applying an electrical signal to a neural structure of a patient; delivering a drug to a patient; or cooling a neural structure of a patient. When the treatment comprises applying an electrical signal to a portion of a neural structure of a patient, the neural structure may be at least one of a portion of a brain structure of the patient, a portion of a cranial nerve of a patient, a portion of a spinal cord of a patient, a portion of a sympathetic nerve structure of the patient, a portion of a parasympathetic nerve structure of the patient, and/or a portion of a peripheral nerve of the patient.

The above methods can be performed alone. In one embodiment, the above methods can be performed in combination with a continuous or open-loop therapy for epilepsy. In one embodiment, the above methods are performed to take action in response to an indication of a state change, and at all or most other times, a chronic therapy signal is applied to a target structure in the patient's body. In one embodiment, the target structure is a cranial nerve, such as the vagus nerve.

Although not limited to the following, an exemplary system capable of implementing embodiments of the present invention is described below. FIG. 1 depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511, issued Dec. 25, 1990 to Reese S. Terry, Jr. Lead assembly 122 may be secured, while retaining the ability to flex with movement of the chest and neck, by a suture connection to nearby tissue (not shown).

In alternative embodiments, the electrode assembly 125 may comprise temperature sensing elements, blood pressure sensing elements, and/or heart rate sensor elements. Other sensors for other body parameters may also be employed. Both passive and active stimulation may be combined or delivered by a single IMD according to the present invention. Either or both modes may be appropriate to treat a specific patient under observation.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Figure 2A:
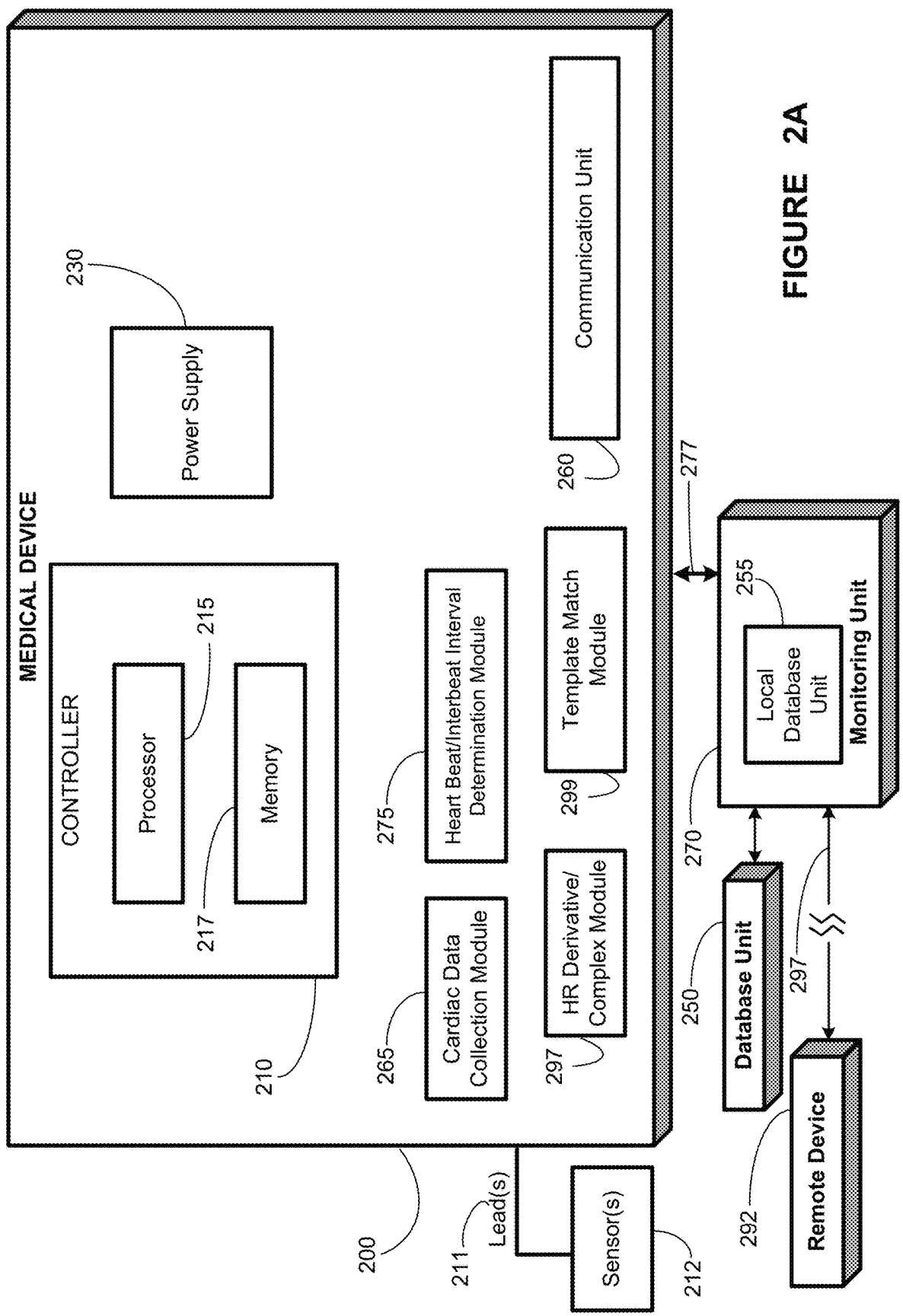
FIG. 2A is a block diagram of a medical device system that includes a medical device and an external unit, in accordance with one illustrative embodiment of the present invention.

Turning now to FIG. 2A, a block diagram depiction of a medical device 200 is provided, in accordance with one illustrative embodiment of the present invention.

In some embodiments, the medical device 200 may be implantable (such as implantable electrical signal generator 110 from FIG. 1), while in other embodiments the medical device 200 may be completely external to the body of the patient.

The medical device 200 (such as generator 110 from FIG. 1) may comprise a controller 210 capable of controlling various aspects of the operation of the medical device 200. The controller 210 is capable of receiving internal data or external data, and in one embodiment, is capable of causing a stimulation unit 220 (FIG. 2B) to generate and deliver an electrical signal to target tissues of the patient's body for treating a medical condition. For example, the controller 210 may receive manual instructions from an operator externally, or may cause the electrical signal to be generated and delivered based on internal calculations and programming. In other embodiments, the medical device 200 does not comprise a stimulation unit 220 (FIG. 2A). In either embodiment, the controller 210 is capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

Figure 2B:
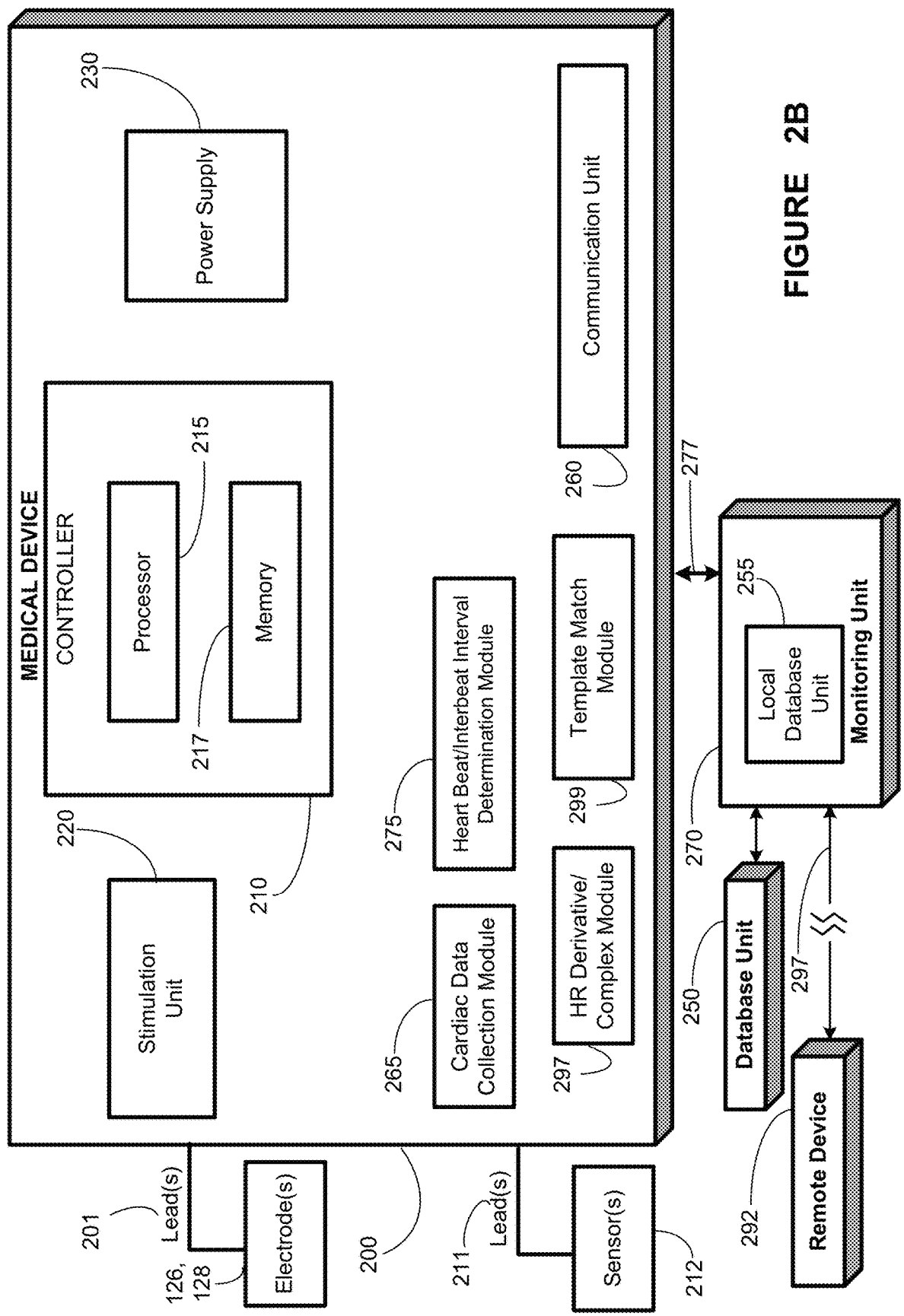
FIG. 2B is a block diagram of a medical device system that includes a medical device and an external unit, in accordance with one illustrative embodiment of the present invention.

As stated above, in one embodiment, the medical device 200 may also comprise a stimulation unit 220 capable of generating and delivering electrical signals to one or more electrodes 126, 128 via leads 201 (FIG. 2B). A lead assembly such as lead assembly 122 (FIG. 1) may be coupled to the medical device 200. Therapy may be delivered to the leads 201 comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering electrical signals over the leads 201 comprising the lead assembly 122. As should be apparent, in certain embodiments, the medical device 200 does not comprise a stimulation unit 220, lead assembly 122, or leads 201.

In other embodiments, a lead 201 is operatively coupled to an electrode, wherein the electrode is adapted to couple to at least one of a portion of a brain structure of the patient, a cranial nerve of a patient, a spinal cord of a patient, a sympathetic nerve structure of the patient, or a peripheral nerve of the patient.

The medical device 200 may also comprise a power supply 230. The power supply 230 may comprise a battery, voltage regulators, capacitors, etc., to provide power for the operation of the medical device 200, including delivering the therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 is capable of providing transmission and reception of electronic signals to and from a monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. The sensor(s) 212 are capable of receiving signals related to a physiological parameter, such as the patient's heart beat, blood pressure, and/or temperature, and delivering the signals to the medical device 200. In one embodiment, the sensor(s) 212 may be the same as implanted electrode(s) 126, 128 (FIG. 1). In other embodiments, the sensor(s) 212 are external structures that may be placed on the patient's skin, such as over the patient's heart or elsewhere on the patient's torso.

In one embodiment, the medical device 200 may comprise a cardiac data collection module 265 that is capable of collecting cardiac data comprising fiducial time markers of each of a plurality of heart beats. The cardiac data collection module 265 may also process or condition the cardiac data. The cardiac data may be provided by the sensor(s) 212. The cardiac data collection module 265 may be capable of performing any necessary or suitable amplifying, filtering, and performing analog-to-digital (A/D) conversions to prepare the signals for downstream processing. The cardiac data collection module, in one embodiment, may comprise software module(s) that are capable of performing various interface functions, filtering functions, etc., to process fiducial time markers of each of a plurality of heart beats. In another embodiment the cardiac data collection module 265 may comprise hardware circuitry that is capable of performing these functions. In yet another embodiment, the cardiac data collection module 265 may comprise hardware, firmware, software and/or any combination thereof. A more detailed illustration of the cardiac data collection module 265 is provided in FIG. 3A and accompanying description below.

The cardiac data collection module 265 is capable of collecting cardiac data comprising fiducial time markers of each of a plurality of candidate heart beats and providing the collected cardiac data to a heart beat/interval determination module 275. Based upon the signals processed by the cardiac data collection module 265, the heart beat/interval determination module 275 may calculate an interbeat interval from a consecutive pair of the fiducial time markers and store such interbeat interval or forward it on for further processing/analysis. The heart beat/interval determination module 275 may comprise software module(s) that are capable of performing various interface functions, filtering functions, etc., to calculate interbeat intervals. In another embodiment the heart beat/interval determination module 275 may comprise hardware circuitry that is capable of performing these functions. In yet another embodiment, the heart beat/interval determination module 275 may comprise hardware, firmware, software and/or any combination thereof. Further description of the heart beat/interval determination module 275 is provided in FIG. 3B and accompanying description below.

The heart beat/interval determination module 275 is capable of calculating an interbeat interval and providing the interbeat interval to the heart rate/heart rate variability (HRV)/complex module 297. Based upon one or more interbeat intervals received from the heart beat/interval determination module 275, and/or signals of sufficient sampling rate to provide information regarding the heart beat complex received from the cardiac data collection module 265, the HR derivative/complex module 297 determines at least one or more of an heart rate (such as from an interbeat interval determined from a consecutive pair of fiducial time markers), a heart rate variability (such as from two consecutive interbeat intervals determined from fiducial time markers), or at least a portion of a heart beat complex.

The HR derivative/complex module 297 may comprise software module(s) that are capable of performing various interface functions, filtering functions, etc., to calculate the various values. In another embodiment the HR derivative/complex module 297 may comprise hardware circuitry that is capable of performing these functions. In yet another embodiment, the HR derivative/complex module 297 may comprise hardware, firmware, software and/or any combination thereof. Further description of the HR derivative/complex module 297 is provided in FIG. 3E and accompanying description below.

The HR derivative/complex module 297 is capable of forwarding the calculated information to template match module 299. Based upon the information received by the template match module 299, it performs any operations desired to indicate a state change. For example, the template match module 299 may indicate a state change based on one or more of a heart rate shape matching an appropriate state change template, an HRV shape matching an appropriate state change template, a portion or more of a heart beat complex failing to match a reference heart beat complex template, or two or more of the foregoing. The template match module 299 may comprise software module(s) that are capable of performing various interface functions, filtering functions, etc., to indicate a state change. In another embodiment the template match module 299 may comprise hardware circuitry that is capable of performing these functions. In yet another embodiment, the template match module 299 may comprise hardware, firmware, software and/or any combination thereof. Further description of the template match module 299 is provided in FIG. 3F and accompanying description below.

In addition to components of the medical device 200 described above, an implantable medical system may comprise a storage unit to store an indication of at least one of state change or an increased risk of a state change. The storage unit may be the memory 217 of the medical device 200, another storage unit of the medical device 200, or an external database, such as the local database unit 255 or a remote database unit 250. The medical device 200 may communicate the indication via the communications unit 260. Alternatively or in addition to an external database, the medical device 200 may be adapted to communicate the indication to at least one of a patient, a caregiver, or a healthcare provider.

In various embodiments, one or more of the units or modules described above may be located in a monitoring unit 270 or a remote device 292, with communications between that unit or module and a unit or module located in the medical device 200 taking place via communication unit 260. For example, in one embodiment, one or more of the cardiac data collection module 265, the heart beat/interval determination module 275, the HR derivative/complex module 297, or the template match module 299 may be external to the medical device 200, e.g., in a monitoring unit 270. Locating one or more of the cardiac data collection module 265, the heart beat/interval determination module 275, the HR derivative/complex module 297, or the template match module 299 outside the medical device 200 may be advantageous if the calculation(s) is/are computationally intensive, in order to reduce energy expenditure and heat generation in the medical device 200 or to expedite calculation.

The monitoring unit 270 may be a device that is capable of transmitting and receiving data to and from the medical device 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 2. This may occur using, e.g., wand 155 (FIG. 1) to communicate by RF energy with an implantable signal generator 110. Alternatively, the wand may be omitted in some systems, e.g., systems in which the MD 200 is non-implantable, or implantable systems in which monitoring unit 270 and MD 200 operate in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient parameter data acquired from a patient's body, therapy parameter data, state change severity data, and/or therapeutic efficacy data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting thresholds for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2A or FIG. 2B, may comprise hardware units, software units, firmware units, or any combination thereof. Additionally, one or more blocks illustrated in FIG. 2A-B may be combined with other blocks, which may represent circuit hardware units, software algorithms, etc. Additionally, any number of the circuitry or software units associated with the various blocks illustrated in FIG. 2A-B may be combined into a programmable device, such as a field programmable gate array, an ASIC device, etc.

Figure 3A:
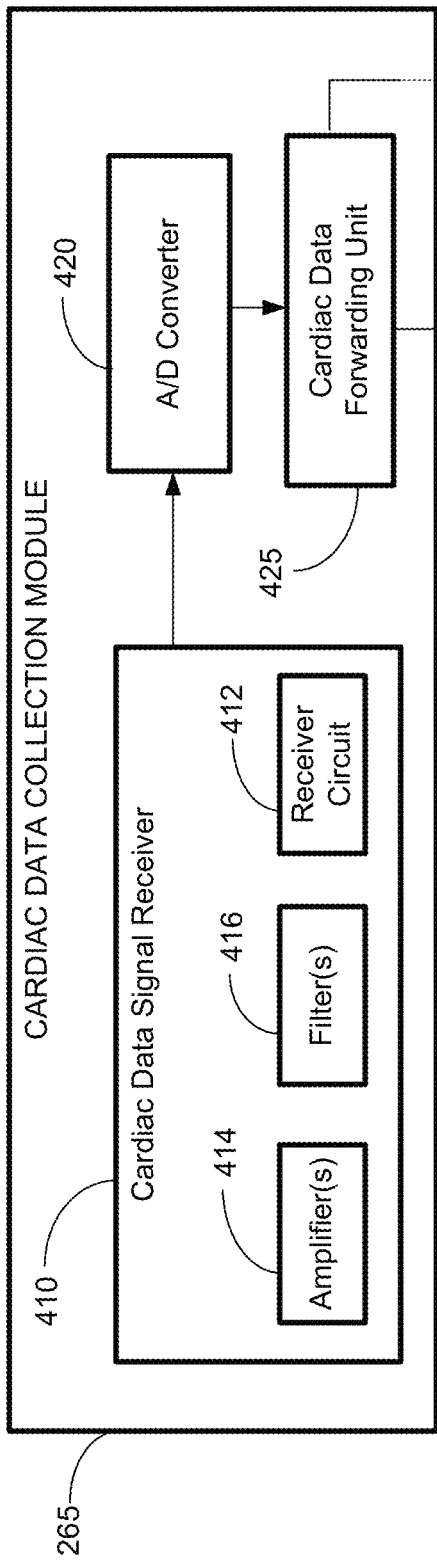
FIG. 3A is a stylized block diagram of a cardiac data collection module of a medical device, in accordance with one illustrative embodiment of the present invention.

Turning now to FIG. 3A, a more detailed stylized depiction of the cardiac data collection module 265 of FIG. 2, in accordance with one illustrative embodiment of the present invention is depicted. In one embodiment, the cardiac data collection module 265 comprises a cardiac data signal receiver 410, an analog-to-digital converter (A/D Converter) 420, and a cardiac data forwarding unit 425. The cardiac data signal receiver 410 is capable of receiving the signals from the sensor(s) 212 via receiver circuit 412. The signal that is received by the receiver circuit 412 is processed and filtered to enable the data to be further analyzed and/or processed for determining cardiac data, such as that described above.

The cardiac data signal receiver 410 may comprise amplifier(s) 414 and filter(s) 416. The amplifiers 414 are capable of buffering and amplifying the input signals received by the receiver circuit 412. In many cases, the heart beat signal may be attenuated and may be characterized by significantly low amplitude responses and signal noise. The amplifier(s) 414 are capable of buffering (amplification by unity) and amplifying the signals for further processing. In one embodiment, the amplifier 414 may comprise op amp circuit(s), digital amplifier(s), buffer amplifiers, and/or the like.

The cardiac data signal receiver 410 may also comprise one or more filters 416. The filters 416 may comprise analog filter(s), digital filter(s), filters implemented by digital signal processing (DSP) means or methods, etc. The amplified and buffered signal may be filtered to remove various noise signals residing on the signal. The filter 416, for example, is capable of filtering out various noise signals caused by external magnetic fields, electrical fields, noise resulting from physiological activity, etc. Signal noise due to breathing or other signals produced by the patient's body may be filtered.

The cardiac data signal receiver 410 provides amplified, filtered signals to the A/D converter 420. The A/D converter 420 performs an analog-to-digital conversion for further processing. The A/D converter 420 may be one type of a plurality of converter types with various accuracies, such as an 8-bit converter, a 12-bit converter, a 24-bit converter, a 32-bit converter, a 64-bit converter, a 128-bit converter, a 256-bit converter, etc. The converted digital signal is then provided to a cardiac data forwarding unit 425. In an alternative embodiment, the A/D conversion may be performed prior to filtering or signal processing of the heart beat signal. The converted digital signal is then provided to a cardiac data forwarding unit 425.

The cardiac data forwarding unit 425 is capable of organizing, correlating, stacking, and otherwise processing the digitized, buffered, and filtered cardiac data and forwarding it to the heart beat/interval determination module 275, and/or directly to the HR derivative/complex module 297.

Figure 3B:
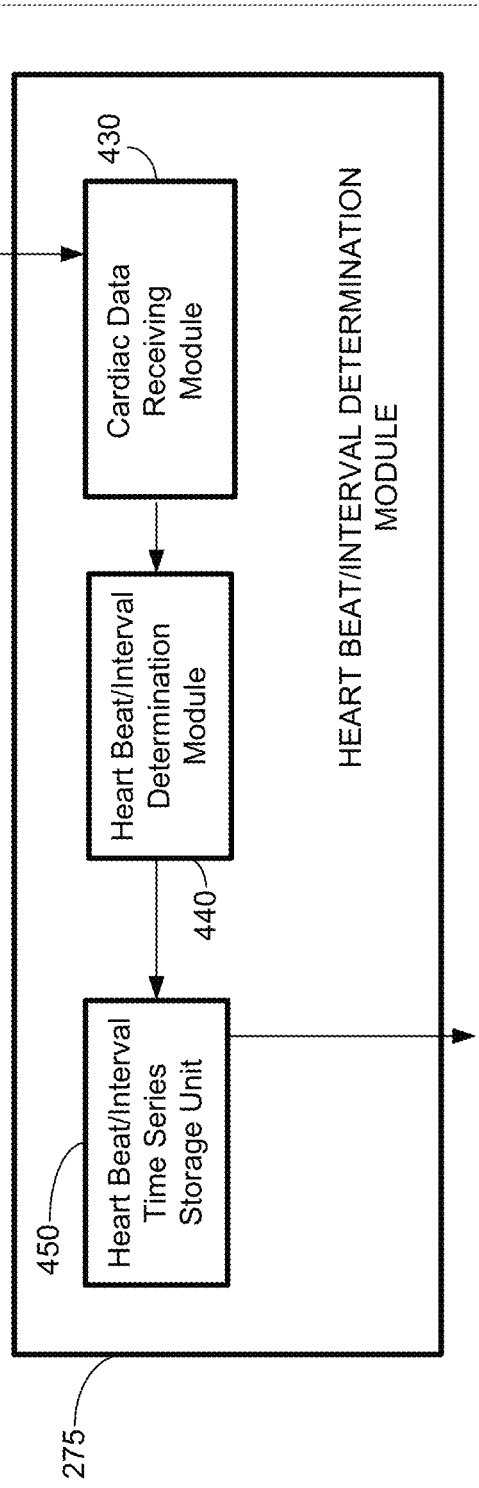
FIG. 3B is a stylized block diagram of a heart beat/interval determination module of a medical device, in accordance with one illustrative embodiment of the present invention.

Turning now to FIG. 3B, a more detailed stylized depiction of the heart beat/interval determination module 275 of FIG. 2, in accordance with one illustrative embodiment of the present invention, is depicted. The heart beat/interval determination module 275 may comprise a cardiac data receiving module 430, for receiving a time stamp sequence of candidate heart beats, a heart beat/interval determination module 440, and a heart beat/interval time series storage unit 450. The heart beat/interval determination module 275 may determine interbeat intervals for adjacent candidate heart beats as they appear in the time series of signals via the cardiac data receiving module 430. For example, cardiac data receiving module 430 may characterize certain data points in the time series of signals as being fiducial time markers corresponding to the start, the peak, or the end of an R-wave of a patient's cardiac cycle.

Once fiducial time markers are determined from the time series of signals, the heart beat/interval determination module 440 may determine the interval between consecutive beats ("interbeat interval") and forward this information to heart beat/interval time series storage 450, which may store one or both of a time stamp series associated with fiducial markers indicating of an individual heart beat and a time stamp series of adjacent interbeat intervals. In some embodiments, the heart beat/interval determination module 440 may calculate a heart rate, heart rate variability (HRV), or at least a portion of a heart beat complex. In other embodiments, heart beat/interval determination module 440 may calculate a heart rate, heart rate variability (HRV), or both.

Turning now to FIG. 3C, a more detailed stylized depiction of the HR derivative/complex module 297 of FIG. 2, in accordance with one illustrative embodiment of the present invention, is depicted. In one embodiment, the HR derivative/complex module 297 may receive various cardiac data indicative from the cardiac data collection module 265 or the heart beat/interval determination module 275. In the embodiment depicted in FIG. 3C, the HR derivative/complex module 297 comprises units that perform various calculations, for example, a heart rate calculation unit 569 may determine a heart rate from some or all interbeat intervals and/or pairs of heart beats collected and/or identified by modules 265 or 275. Certain embodiments of the invention may also include a heart rate variability unit 571 which determines an HRV value from some or all interbeat intervals and/or pairs of heart beats collected and/or identified by modules 265 or 275, and/or a heart beat complex unit 572 which analyzes one or more portions of a heart beat complex, e.g., relative R-wave and P-wave amplitudes, P-wave to R-wave temporal separations, or the like. Of course, one or more of units 569, 571, and 572 may be omitted, if desired.

The HR derivative/complex module 297 need not perform all steps 569-572. Any steps the HR derivative/complex module 297 performs may be in any order, not necessarily that shown.

Although the heart rate calculation unit 569, the heart rate variability unit 571, and the heart beat complex unit 572 are shown in FIG. 3C as components of HR derivative/complex module 297, in various other embodiments, one or more of these units can be included in other modules.

Turning now to FIG. 3D, a more detailed stylized depiction of the template match module 299 of FIG. 2, in accordance with one illustrative embodiment of the present invention, is depicted. The template match module 299 may receive various data from the HR derivative/complex module 297, including, for example, one or more a heart rate shape characteristics, one or more HRV shape characteristics, information regarding one or more portions of a heart beat complex, etc. Based upon data from the HR derivative/complex module 297, the template match module 299 is capable of indicating a state change, such as described above.

In the exemplary depiction shown in FIG. 3D, data received from the HR derivative/complex module 297 is forwarded to a template comparison unit 587, which determines whether one or more of the heart rate shape, HRV shape, or portion of the heart beat complex matches a relevant template. The determination of a match can be performed by known mathematical techniques, such as matched filtering, or the like. A signal indicative of the occurrence of a state change is provided by state change indication unit 589 if the template comparison is indicative of a state change, such as a seizure.

If a state change is identified by template match module 299, in one embodiment, a response may be implemented, such as those described by U.S. patent application Ser. No. 12/770,562, filed Apr. 29, 2010; Ser. No. 12/771,727, filed Apr. 30, 2010; and Ser. No. 12/771,783, filed Apr. 30, 2010.

Figure 4:
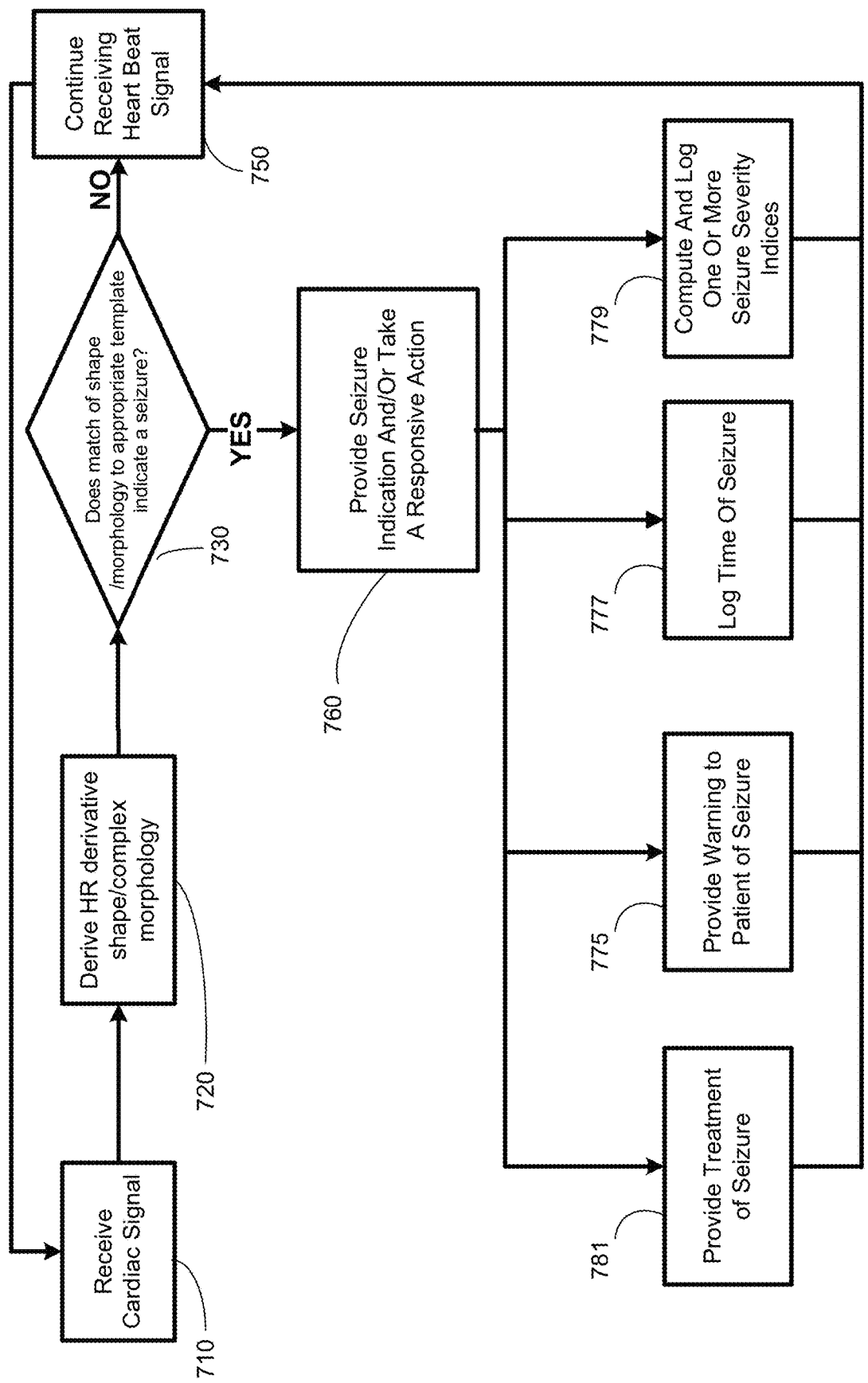
FIG. 4 illustrates a flowchart depiction of a method for detecting a state change and taking one or more responsive actions, in accordance with an illustrative embodiment of the present invention.

Turning now to FIG. 4, a stylized flowchart depiction of detecting one particular type of state change, namely, a seizure, in accordance with one illustrative embodiment of the present invention, is provided. The medical device 200 receives a cardiac signal (block 710). In specific embodiments, the cardiac data collection module 265 (FIGS. 2 and 3A) of the medical device 200 receives the cardiac signal. After performing buffering, amplification, filtering, and A/D conversion of the cardiac signal, the heart beat/interval determination module 275 and/or HR derivative/complex module 297 processes the heart beat signal to derive HR derivative shapes or heart beat complex morphology (block 720). From the derived shapes or characteristics, it is decided from one or more template matching operations if a state change is indicated (block 730). This decision may be performed by template match module 299.

Based upon the decision (block 730), if no state change is indicated, the medical device 200 continues to receive the heart beat signal (block 750, returning flow to block 710).

However, if a state change is indicated in block 730, the medical device 200 or an external unit 270 may provide an indication of the state change occurrence and/or take a responsive action (block 760), such as providing a warning to the patient or his or her caregivers, physician, etc. (block 775); logging a time of state change (block 777); computing and optionally logging one or more state change severity indices (block 779); and/or providing treatment of the state change (block 781). More details on logging, warning, computing seizure severity, and providing treatment are provided in U.S. patent application Ser. No. 12/770,562, filed Apr. 29, 2010; Ser. No. 12/771,727, filed Apr. 30, 2010; Ser. No. 12/771,783, filed Apr. 30, 2010; and Ser. No. 12/756,065, filed Apr. 7, 2010.

The above methods may be performed by a computer readable program storage device encoded with instructions that, when executed by a computer, perform the method described herein.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

In various embodiments, the present invention relates to the subject matter of the following numbered paragraphs:

34. A method for identifying a state change template from cardiac data, comprising:

obtaining a time series of cardiac data from a patient during a first time window;

determining a time of occurrence of at least one state change suffered by said patient during said first time window; and either (i) determining at least one state change template in the time series of cardiac data within the first time window and timewise correlated with the at least one state change, wherein the at least one state change template comprises at least one characteristic selected from a number of phases relative to a reference heart rate parameter, a number of extrema, area under the curve of at least one phase, a number of directions of change, a number of positive phases relative to said reference heart rate parameter, or a number of negative phases relative to said reference heart rate parameter, or (ii) determining at least one reference heart beat complex template in said time series of cardiac data within said first time window and not timewise correlated with said at least one state change.

35. The method of numbered paragraph 34, wherein said cardiac data comprises heart rate data, heart rate variability data, or heart rate volatility data.

36. The method of numbered paragraph 34, wherein said cardiac data comprises at least a portion of each of a plurality of heart beat complexes.

37. The method of numbered paragraph 34, wherein said at least one characteristic comprises at least one of the amplitude of at least one phase, the duration of at least one phase, the valence (positive or negative) of at least one phase, the area under the curve of at least one phase, at least one slope of at least one phase, the arc length of at least one phase, the number of extrema in at least one phase, and the sharpness of the extrema of at least one phase.

38. A method for obtaining a state change template indicative of an occurrence of a state change of interest, comprising:
obtaining a first time series of cardiac data from a patient, the first time series not associated with said state change of interest;
determining at least one reference heart rate parameter from said first time series of cardiac data;
obtaining a second time series of cardiac data from said patient, the second time series being associated with said state change of interest;
determining at least one property of said heart rate derivative, said property comprising at least one of a number of phases relative to said reference heart rate parameter, the perimeter of at least one phase, a number of extrema of said heart rate derivative, the sharpness of said extrema, a number of directions of change of said heart rate derivative, an area under the curve of at least one phase, a number of positive phases, or a number of negative phases; and
determining that the at least one property of said heart rate derivative of the state of interest is different from the same at least one property of the heart rate derivative not associated with the state of interest
obtaining a state change template associated with said state change of interest and comprising said at least one property, from said heart rate derivative and using it as a matched filter to detect said state change.

39. The method of numbered paragraph 38, wherein the at least one property of said pattern comprises a shape of said pattern, a time of occurrence of said pattern, a time elapsed between occurrences of said pattern, and an association of said pattern with a state change of a body organ.

40. The method of numbered paragraph 39, wherein said at least one property of said pattern is an association of said pattern with a state change of the brain.

41. The method of numbered paragraph 40, wherein said state change of the brain is a epileptic seizure.

42. The method of numbered paragraph 38, wherein said heart rate derivative is heart rate.

43. The method of numbered paragraph 38, wherein said heart rate derivative is heart rate variability or heart rate volatility.

44. A method for indicating an occurrence of a state change, comprising:
providing a first template comprising at least one of a microscopic state change template, a mesoscopic state change template, and a macroscopic state change template;
obtaining a time series of cardiac data from a patient;
determining a first cardiac data derivative shape from said time series of cardiac data; and,
indicating an occurrence of a state change based upon a determination that said first cardiac data derivative shape matches said first template.

45. The method of numbered paragraph 44, further comprising:
providing a second template comprising at least one of said microscopic state change template, said mesoscopic state change template, and said macroscopic state change template, wherein said second template is not based upon a state change template included in said first template;
determining a second cardiac data derivative shape from said time series of cardiac data;
and wherein said indicating is based upon a determination that said first cardiac data derivative shape matches said first template and said second cardiac data derivative shape matches said second template.

46. The method of numbered paragraph 44, wherein said determination comprises using a matched filter on a moving window of said first cardiac data derivative, calculating a time series of outputs of said matched filter, and declaring said match if said time series of outputs is substantially equal to a time series of expected output values.

101. A method for indicating an occurrence of a state change, comprising:
obtaining a time series of cardiac data from a patient;
selecting at least one parameter from said cardiac data time series;
determining the magnitude, duration, direction and rate of change of said parameter during a reference state wherein said parameter comprises at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;
indicating the occurrence of a state change when at least one of said values is greater or lower than at least one reference state parameter value, e.g., for a certain time period.

102. The method of numbered paragraph 101 wherein the parameters' values are treated as phases and extrema endowed with shape, curvature, arc length and inflection points;
indicating the occurrence of a state change when at least one of the parameters' values is greater or lower than at least one reference state parameter values, e.g., for a certain time period.

103. The method of numbered paragraph 101 wherein the cardiac data parameter's value's temporal scale is macroscopic.

104. The method of numbered paragraph 101 wherein the cardiac data parameter's value's temporal scale is mesoscopic.

105. The method of numbered paragraph 101 wherein the cardiac data parameter's value's temporal scale is microscopic.

106. A method for indicating an occurrence of a state change, comprising:
obtaining a time series of cardiac data from a patient during a reference state;
selecting at least one parameter from said cardiac data during said reference state wherein said reference parameter comprises at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

constructing a reference template using said at least one reference parameter value and using said template as a reference matched filter;

indicating an occurrence of a state change based upon a determination that the output of said at least one reference matched filter reaches a value outside the range of values characteristic of the reference state.

107. The method of numbered paragraph 106 wherein the reference matched filter's scale is macroscopic.

108. The method of numbered paragraph 106 wherein the reference matched filter's scale is mesoscopic.

109. The method of numbered paragraph 106 wherein the reference matched filter's scale is microscopic.

110. A method for indicating an occurrence of a state change, comprising:

obtaining a time series of cardiac data from a patient during a non-reference state;

selecting at least one parameter from said cardiac data during said non-reference state wherein said non-reference parameter comprises at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

constructing a non-reference template using said at least one non-reference parameter value and using said non-reference template as a non-reference matched filter;

indicating an occurrence of a state change based upon a determination that the output of said at least one non-reference matched filter reaches a value characteristic of the non-reference state values.

111. The method of numbered paragraph 110, wherein the non-reference matched filter's scale is macroscopic.

112. The method of numbered paragraph 110, wherein the non-reference matched filter's scale is mesoscopic.

113. The method of numbered paragraph 110, wherein the non-reference matched filter's scale is microscopic.

114. A method for indicating an occurrence of a state change, comprising:

obtaining a time series of cardiac data from a patient;

selecting at least one reference parameter and at least one non-reference parameter from said cardiac data wherein said parameters comprise at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

constructing a reference template using said at least one reference parameter value and using said reference template as a reference matched filter;

constructing a non-reference template using said at least one non-reference parameter value and using said non-reference template as a non-reference matched filter;

indicating an occurrence of a state change based upon a determination that the output of said at least one reference matched filter reaches a value outside the values characteristic of the reference state values and the output of said at least one non-reference matched filter reaches a value characteristic of the non-reference state values.

115. The method of numbered paragraph 114, wherein the scales of the reference and of the non-reference matched filters are macroscopic.

116. The method of numbered paragraph 114, wherein the scales of the reference and of the non-reference matched filters are mesoscopic.

117. The method of numbered paragraph 114, wherein the scales of the reference and of the non-reference matched filters are microscopic.

118. A method for obtaining a state change template indicative of an occurrence of a state change of interest, comprising:

obtaining a first time series of cardiac data from a patient, the first time series not associated with said state change of interest;

determining at least one parameter from said first time series of cardiac data wherein said parameters comprise at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

obtaining a second time series of cardiac data from said patient, the second time series being associated with said state change of interest;

determining at least one parameter from said second time series of cardiac data wherein said parameters comprise at least one of a heart rate, a heart rate variability, a heart rate volatility, a characteristic of the heart's electrical beat, a characteristic of the heart's beat sounds, a characteristic of the heart's beat contractility and a characteristic of the heart's beat generated pressure;

determining that the at least one parameter from said second time series of cardiac data associated with a state change of interest is different from the same at least one parameter of the first time series of cardiac data not associated with a state change of interest;

obtaining a state change template associated with said state change of interest and comprising said at least one property;

using said state change template as a matched filter to detect similar state changes.

119. The method of numbered paragraph 118, wherein the scale of said template and matched filter associated with a state change of interest is macroscopic.

120. The method of numbered paragraph 118, wherein the scale of said template and matched filter associated with a state change of interest is mesoscopic.

121. The method of numbered paragraph 118, wherein the scale of said template and matched filter associated with a state change of interest is microscopic.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method for detecting an occurrence of a seizure, the method comprising:

obtaining via one or more medical devices a time series of cardiac data from a patient;

selecting via the one or more medical devices at least one parameter from the cardiac data time series;

selecting a time period;

selecting a time scale for the selected time period where the selected time scale is one of a macroscopic time scale, a mesoscopic time scale, or a microscopic time scale;

determining via the one or more medical devices a rate of change of a heart rate volatility;

comparing a value relating to heart rate volatility to a reference state value for the selected time period; and indicating the occurrence of the seizure when the value relating to the heart rate volatility is different than the reference state value for the selected time period;

wherein the value includes an inflection point.

2. The method of claim 1, wherein the time series of cardiac data comprises at least 300 seconds of data.

3. The method of claim 1, wherein the time series of cardiac data comprises from about 10 seconds to about 300 seconds of data.

4. A non-transitory computer readable program storage unit encoded with instructions that, when executed by a computer, perform a method for indicating an occurrence of a seizure, the non-transitory computer readable program unit being part of a medical device, the method comprising:

obtaining via the medical device a time series of cardiac data from a patient;

selecting via the medical device at least one parameter from the cardiac data time series;

determining via the medical device a rate of change of a heart rate volatility;

comparing a value relating to heart rate volatility to a reference state value for the selected time period; and indicating the occurrence of the seizure when the value relating to the heart rate volatility is different than the reference state value for a selected time period;

wherein the value includes an inflection point.

5. The non-transitory computer readable program storage unit of claim 4, wherein the time series of cardiac data comprises at least 300 seconds of data.

6. The non-transitory computer readable program storage unit of claim 4, wherein the time series of cardiac data comprises from about 10 seconds to about 300 seconds of data.

* * * * *